US006653318B1

(12) United States Patent
Cheng et al.

(10) Patent No.: US 6,653,318 B1
(45) Date of Patent: Nov. 25, 2003

(54) 5-(E)-BROMOVINYL URACIL ANALOGUES AND RELATED PYRIMIDINE NUCLEOSIDES AS ANTI-VIRAL AGENTS AND METHODS OF USE

(75) Inventors: Yung-Chi Cheng, Woodbridge, CT (US); Chung K. Chu, Athens, GA (US); Ling Li, Hamden, CT (US); Yongseok Chai, Athens, GA (US)

(73) Assignees: Yale University, New Haven, CT (US); The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/358,028

(22) Filed: Jul. 21, 1999

(51) Int. Cl.[7] .................. A61K 31/505; A61K 31/335; A61K 31/34
(52) U.S. Cl. .................. 514/274; 514/256; 514/269; 514/272; 514/467; 514/461
(58) Field of Search .................. 514/50, 51, 274, 514/256, 269, 272, 467, 461

(56) References Cited

U.S. PATENT DOCUMENTS

| | | |
|---|---|---|
| 4,210,638 A | 7/1980 | Greer |
| 4,287,188 A | 9/1981 | Schaeffer |
| 4,542,210 A | 9/1985 | Sakata et al. |
| 4,596,798 A | 6/1986 | Shipman, Jr. et al. |
| 4,652,580 A | 3/1987 | Janssen et al. |
| 4,714,701 A | 12/1987 | Beauchamp |
| 4,777,166 A | 10/1988 | Smith et al. |
| 4,863,906 A | 9/1989 | Rahim et al. |
| 4,963,555 A | 10/1990 | Jones et al. |
| 5,028,596 A | 7/1991 | Purifoy et al. |
| 5,036,071 A | 7/1991 | Johansson et al. |
| 5,036,072 A | 7/1991 | Nakajima et al. |
| 5,041,449 A | 8/1991 | Belleau et al. |
| 5,047,407 A | 9/1991 | Belleau et al. |
| 5,055,458 A | 10/1991 | Bailey et al. |
| 5,079,235 A | 1/1992 | Purifoy et al. |
| 5,086,044 A | 2/1992 | Rideout et al. |
| 5,151,426 A | 9/1992 | Belleau et al. |
| 5,179,104 A | 1/1993 | Chu et al. |
| 5,210,085 A | 5/1993 | Liotta et al. |
| 5,216,142 A | 6/1993 | Horrobin et al. |
| 5,248,776 A | 9/1993 | Chu et al. |
| 5,270,315 A | 12/1993 | Belleau et al. |
| 5,276,020 A | 1/1994 | Horrobin et al. |
| 5,356,882 A | 10/1994 | Walker et al. |
| 5,424,295 A | 6/1995 | Krenitsky et al. |
| 5,466,806 A | 11/1995 | Belleau |
| 5,521,163 A | 5/1996 | Walker et al. |
| 5,565,438 A | 10/1996 | Chu et al. |
| 5,597,824 A | 1/1997 | Norbeck et al. |
| 5,602,130 A | 2/1997 | Chandraratna |
| 5,643,891 A | 7/1997 | Rideout et al. |
| 5,683,990 A | 11/1997 | Rideout et al. |
| 5,684,010 A | 11/1997 | Schinazi |
| 5,700,937 A | 12/1997 | Liotta et al. |
| 5,714,516 A | 2/1998 | Harper et al. |
| 5,792,773 A | 8/1998 | Chu et al. |
| 5,840,728 A | 11/1998 | Marquez et al. |
| 5,885,957 A | 3/1999 | Rideout et al. |
| 5,886,013 A | 3/1999 | Rossignol |
| 6,022,876 A | 2/2000 | Chu et al. |

FOREIGN PATENT DOCUMENTS

| | | | |
|---|---|---|---|
| EP | 0 337 713 A | 10/1989 | |
| EP | 0337713 | 10/1989 | |
| EP | 0 572 669 A | 12/1993 | |
| WO | WO 92/10497 | 6/1992 | |
| WO | WO 92/14729 | 9/1992 | |
| WO | WO 94/04154 | 3/1994 | |
| WO | WO 96/07413 | 3/1996 | |
| WO | WO 98 20879 | 5/1998 | |
| WO | WO-98/20879 | * 5/1998 | ......... A61K/31/505 |

OTHER PUBLICATIONS

Bednarski et al., Bioorg. Med. Chem. Lett., (1994), 4(22), 2667–2672.*

Bednarski K et al., Bioorganic & Medicinal Chemistry Letters, Oxford, GB 4 (22) 1994, pp. 2667–2672.

Wilson L J et al., Biooorganic & Medicincal Chemistry Letters, Oxford, GB, 3 (2) 1993, pp. 169–174.

Li Ling et al. Database CA 'Online! Chemical Abstracts Service, Columbus, Ohio, US; 2000 Database accession No. 134:65840 abstract.

Chu et al. "Drug Design and Synthesis of Anti–Hepatitis B Virus Agents", *Antiviral Therapy*, 1(4): pp. 33–38, 1996.

Xu et al. "Improved Synthesis of L–1,3–Dioxolanyl and L–1,3–Oxathiolanyl Acetate from L–Gulose", *Arch. Pharm. Res.*, 17(5): pp. 386–388, 1994.

Wilson et al. The Synthese and Anti–HIV Activity of Pyrimidine Dioxolanyl Nucleosides. Bioorganic & Medicinal Chem. Letters. Feb. 1993, vol. 3, No. 2 pp. 169–174.

Kim et al. L–beta–(2S,4S)–and L–alpha–(2S,4R)–Dioxolanyl Nucleosides as Potential Anti–HIV Agents: Asymmetric Synthesis and Structure–Activity Relationships. J. Medicinal Chem. Mar. 5, 1993, vol. 36, No. 5, pp. 519–528.

Mar et al. Some Nucleoside Analogs With Anti–Human Immunodeficiency Virus Activity Inhibit Replication of Epstein–Barr Virus. Antiviral Research 28 (1995) pp. 1–11.

(List continued on next page.)

*Primary Examiner*—Sreeni Padmanabhan
*Assistant Examiner*—S. Jiang
(74) *Attorney, Agent, or Firm*—Henry D. Coleman; Coleman Sudol Sapone, P.C.

(57) ABSTRACT

The present invention relates to pyrimidine nucleoside compounds and their use to treat viral infections of Varicella Zoster virus and Epstein Barr Virus, as well as cancers which are complications of Epstein Barr virus.

30 Claims, 5 Drawing Sheets

OTHER PUBLICATIONS

Yao et al. Inhibition of Epstein–Barr Virus Replication by a Novel L–Nucleoside, 2'–Fluoro–5–methyl–β–L–arabinofuranosyluracil. Biochemical Pharmacology, 1996, vol. 51, pp. 941–947.

Pai et al. Inhibition of Hepatitis B Virus by a Novel L–Nucleoside, 2'–Fluoro–5–Methyl–β–L–Arabinofuranosyl Uracil. Antimicrobial Agents and Chemotherapy, Feb. 1996, vol. 40, No. 2, pp. 380–386.

Lee et al. Dioxolane Cytosine Nucleosides as Anti–Hepatitis B Agents. Bioorganic & Medicinal Chemistry Letters, Sep. 7, 1995, vol. 5, No. 17, pp. 2011–2014.

Chu et al. Asymmetric Synthesis of Enantiomerically Pure (–)–(1'R,4'R)–Dioxolane–thymine and Its Anti–HIV Activity. Tetrahedron Letters, Jul. 29, 1991, vol. 32, No. 31, pp. 3791–3794.

Kim et al. Asymmetric Synthesis of 1,3–Dioxolane–Pyrimidine Nucleosides and Their Anti–HIV Activity. Journal of Medicinal Chemistry. May 29, 1992, vol.35, No. 11, pp. 1987–1995.

Fields et al. (Editors). Burkitt's Lymphoma. Fields Virology, 1996, Third Edition, vol. 2, Chapter 75, pp. 2419–2420.

Choi et al. In Situ Complexation Directs the Stereochemistry of N–Glycosylation in the Synthesis fo Oxathiolanyl and-Dioxolanyl Nucleoside Analogues. Journal of the American Chemical Society, Nov. 20, 1991, vol. 113, No. 24, pp. 9377–9379.

Berkow et al. (Editors). The Merck Manual of Diagnosis and Therapy, 1992, Sixteenth Edition, pp. 74–86, pp. 203–205, pp. 2282–2285.

* cited by examiner

Scheme 1. Synthesis of L-BVDU

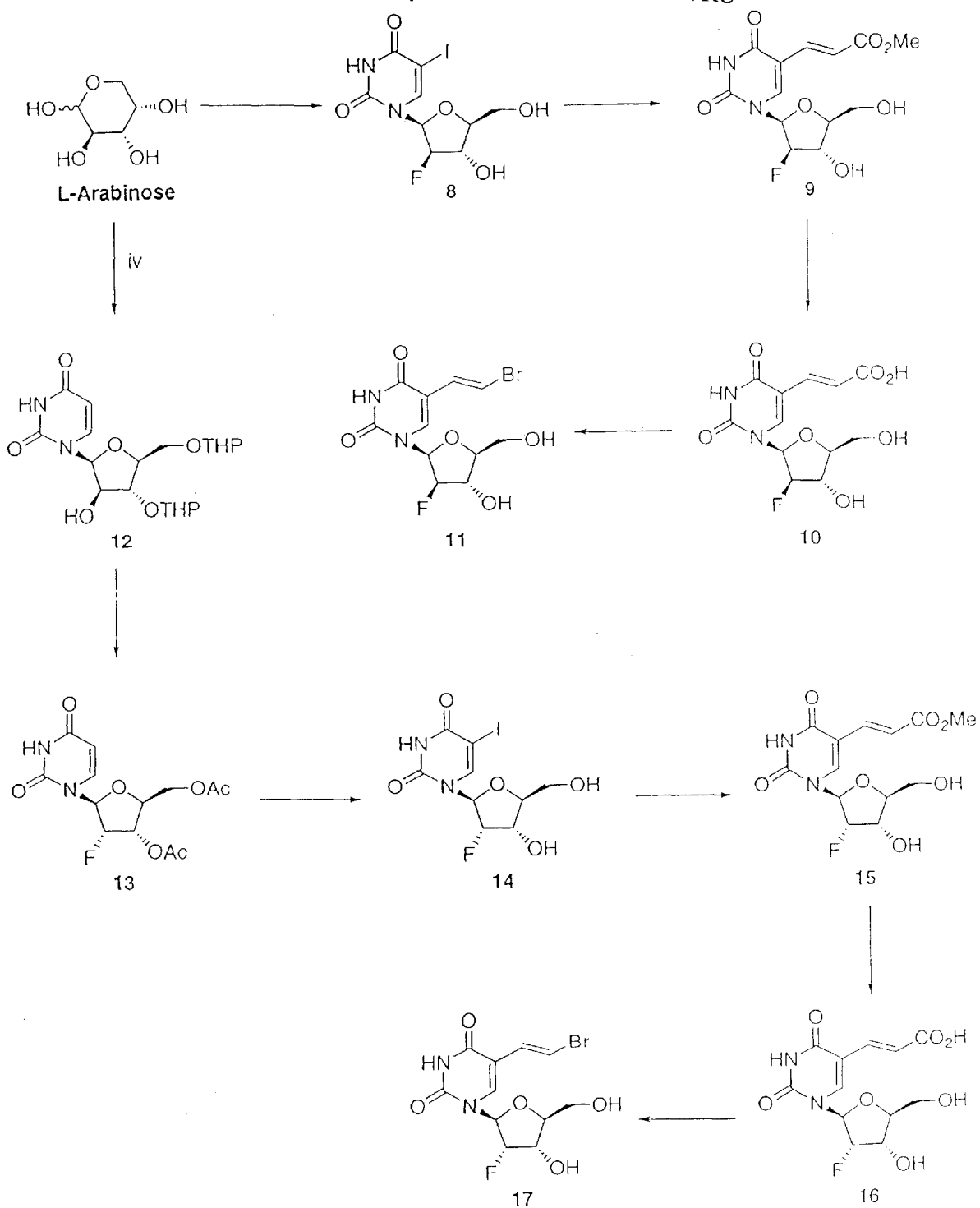
Scheme 2. Synthesis of L-FBVAU and L-FVRU

Scheme 3. Synthesis of 5-BV-SddU
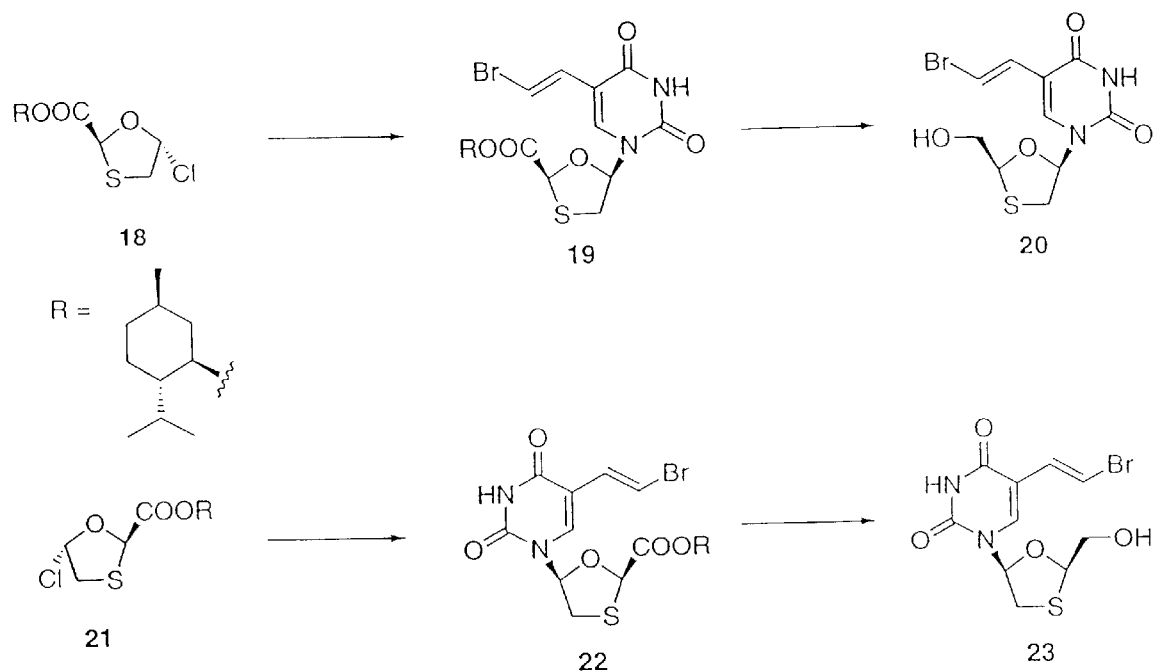

Scheme 4. Synthesis of D-5-BV-OddU
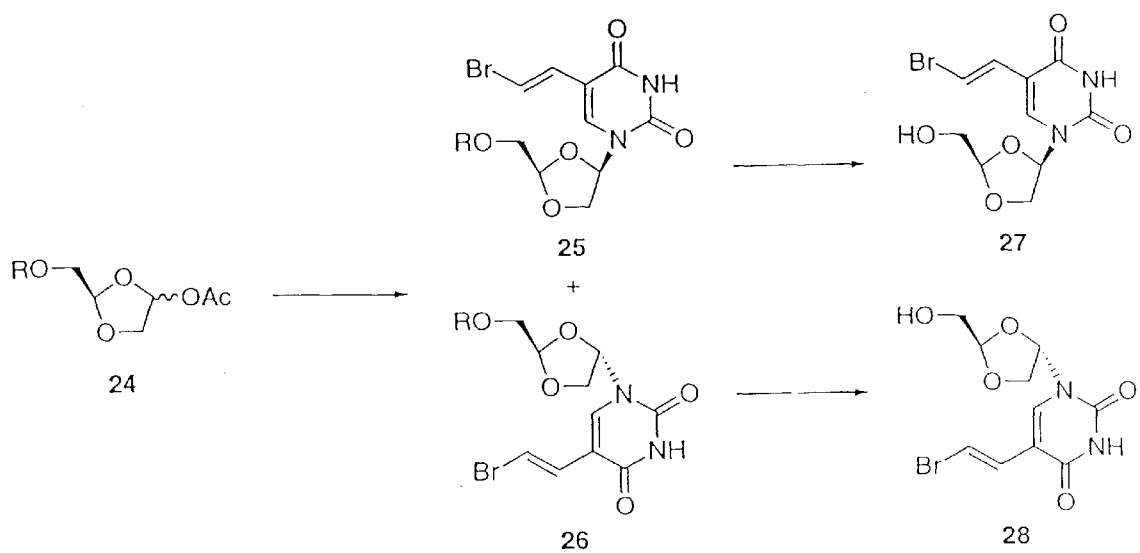

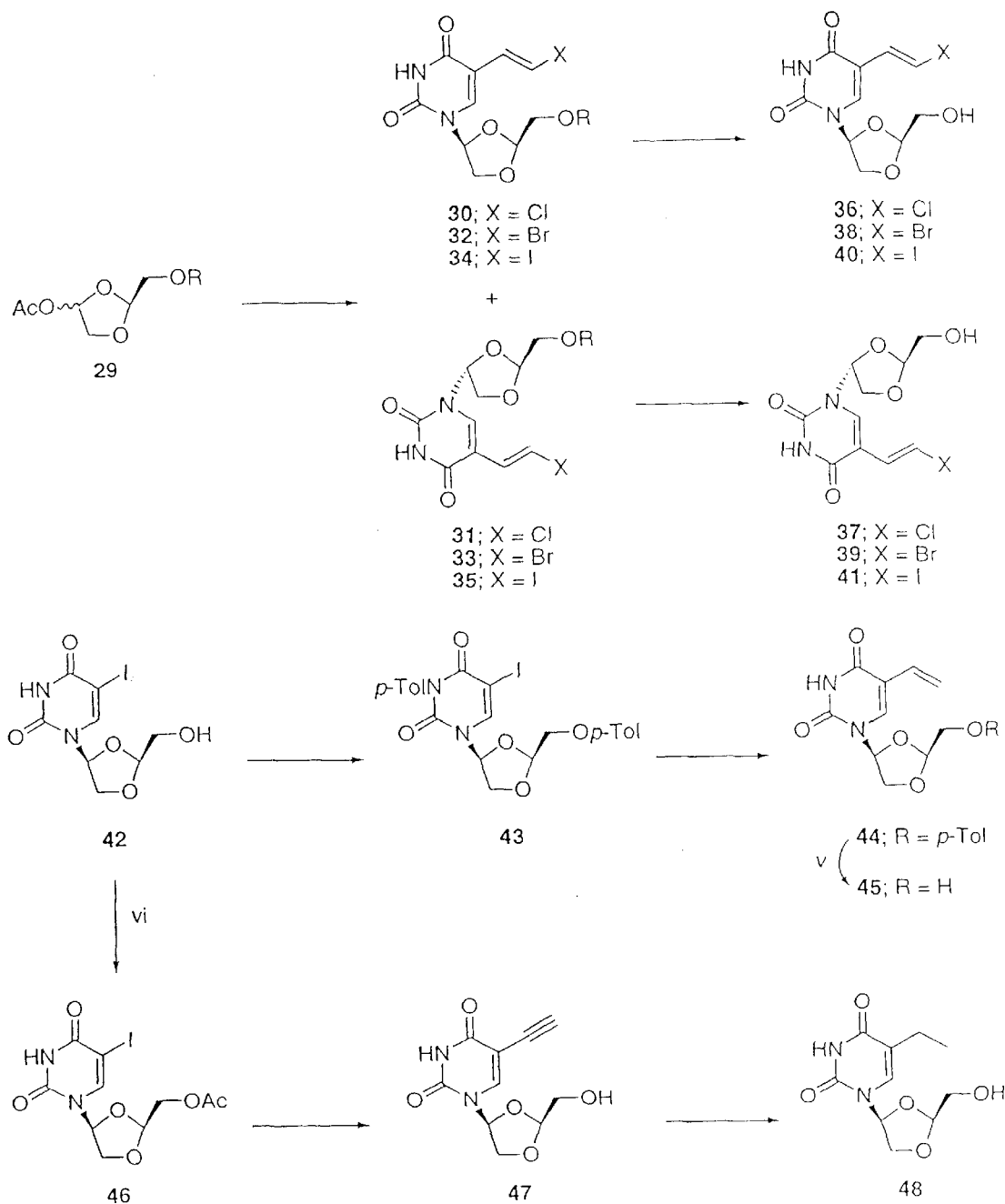
Scheme 5. Synthesis of 5-Substituted L-Dioxolanyl Uracil Analogues

5-(E)-BROMOVINYL URACIL ANALOGUES AND RELATED PYRIMIDINE NUCLEOSIDES AS ANTI-VIRAL AGENTS AND METHODS OF USE

Certain research which gave rise to the present invention was supported by NIH Grant Number AI33655. Consequently, the government retains certain rights in the invention.

FIELD OF THE INVENTION

The present invention relates to pyrimidine nucleoside compounds and their use to treat viral infections of Varicella Zoster Virus, Epstein Barr Virus and Kaposi's Sarcoma virus, also known as HV-8 and related complications of these viral infections. In another aspect of the present invention, the use of one or more nucleoside compound to increase the rentention or the metabolic/catabolic half-life of 5-fluorouracil (FU) in cancer patients is also described.

BACKGROUND OF THE INVENTION

As human bacterial infections have become more manageable and treatable through the use of increasingly available antibiotic agents, viral infections have remained a more difficult and less treatable target. Emphasis in finding agents to treat viral infections has remained a high priority. Problematic virus is Varicella zoster virus, Epstein Barr virus and Kaposi's Sarcoma virus.

Varicella zoster virus (VZV), a member of the herpes virus family, is a main causative agent for a primary infection (varicella and chickenpox) as well as a recurrent disease (zoster and shingles). Snoeck, et al., "Chemotherapy of varicella-zoster virus-infections." *Intl. J. Antimicrob. Agents* 1994, 4, 211–226. The course of varicella is generally benign in immunocompetent patients, however, in immunocompromised patients, particularly patients suffering from the acquired immune deficiency syndrome (AIDS), transplant recipients, and cancer patients, VZV infections can be life-threatening. Snoeck, et al. "Current pharmacological approaches to the therapy of varicella zoster virus infections. A guide to treatment.", *Drugs* 1999, 57, 187–206; and Lee, P. J. and Annunziato, P. "Current management of herpes zoster." *Infections in Medicine* 1998, 15, 709–713.

The current treatment for patients infected with VZV and for immunocompetent patients at risk, such as pregnant women or premature infants, is based on acyclovir (ACV). See, Whitley, R. J. "Therapeutic approaches to varicella-zoster virus infections." *J. Infect. Dis.* 1992, 166, Suppl. 1: 51–57; Shepp, et al. "Treatment of varicella-zoster virus in severely immunocompromised patients: a randomized comparison of acyclovir and vidarabine." *New Engl. J. Med.* 1986, 314, 208–212; Whitley, et al. "Disseminated herpes zoster in the immunocompromised host: a comparative trial of acyclovir and vidarabine." *J. Infect. Dis.* 1992, 165, 450–455. However, the efficacy and low oral bioavailability of ACV (De Miranda and Blum, "Pharmacokinetics of acyclovir after intravenous and oral administration." *J. Antimicrob. Chemother.* 1983, 12, Suppl. B: 29–37), as well as the emergence of drug-resistant virus strains (See, Pahwa, et al. "Continuous varicella-zoster infection associated with acyclovir resistance in a child with AIDS" *J. Am. Med. Assoc.* 1988, 260, 2879–2882; Linnemann, et al. "Emergence of acyclovir-resistant varicella zoster virus in an AIDS patient on prolonged acyclovir therapy." *AIDS* 1990, 4, 577–579; Jacobson, et al. "Acyclovir-resistant varicella zoster virus infection afetr chronic acyclovir therapy in patients with the acquired immunodeficiency syndrome (AIDS)." *Ann. Intern. Med.* 1990, 112, 187–191), have stimulated the development of new compounds for the treatment of VZV infection.

Among the efforts to develop new compounds, (E)-5-(2-bromovinyl)uracil (BVU) analogues, such as (E)-5-(2-bromovinyl)-2'-deoxyuridine (BVDU) and 1-β-D-arabinofuranosyl-(E)-5-(2-bromovinyl)uracil (BVaraU), have been found to exhibit potent anti-VZV activity. See, for example, De Clercq, et al. "(E)-5-(2-Bromovinyl)-2'-deoxyuridine: a potent and selective anti-herpes agent." *Proc. Natl. Acad. Sci. USA* 1979, 76, 2947–2951 and Machida, et al., "Antiherpes-viral and anticellular effects of 1-β-D-arabinofuranosyl-E-5-(2-halogenovinyl)uracils. *Antimicrob. Agents Chemother.* 1981, 20, 47–52. However, metabolic stability of BVDU by pyrimidine nucleoside phosphorylase and, recently, drug interaction of BVaraU with anticancer agent 5-FU, which resulted in death of several patients with cancer and herpes zoster, have been potential drawbacks and limit their use. Desgranges, et al., *Biochem. Pharmacol.* 1983, 32, 3583; David, S., "Deaths bring clinical trials under scrutiny in Japan." *Nature* 1994, 369, 697 and Watabe, et al., "Lethal drug interactions of the new antiviral, sorivudine, with anticancer prodrugs of 5-fluorouracil." *Yakugaku Zasshi* 1997, 117, 910–921. Efforts to address these problems have led to several interesting nucleosides, such as 4'-thio-BVDU and the carbocyclic analog carba BvdU. Dyson, et al. "The synthesis and antiviral activity of some 4'-thio-2'-deoxy nucleoside anlogues." *J. Med. Chem.* 1991, 34, 2782–2786 and Herdewijn, et al., "Synthesis and antiviral activity of the carbocyclic analogues of (E)-5-(2-halovinyl)-2'-deoxyuridines and (E)-5-(2-halovinyl)-2'-deoxycytidines." *J. Med. Chem.* 1985, 28, 550–555. However, the carba derivatives perform very poorly in vivo although they are resistant to degradation and in cell cultures have antiviral activities comparable to those of the parent compounds. Spadari, et al., "5-Iodo-2'-deoxy-L-uridine and (E)-5-(2-bromovinyl)-2'-deoxy-L-uridine: selective phosphorylation by herpes simplex virus type 1 thymidine kinase, antiherpetic activity, and cytotoxicity studies." *Mol. Pharmacol.* 1995, 47, 1231–1238.

L-β-BVOddU was originally discovered by Krzystof, et al. to have inhibitory activity against HSV-1 replication. Although this compound is known, the potential usage for the treatment of VZV has not been reported. See Krzystof, et al., *Bioorganic and Medical Chemistry Letter*. Vol 4 (22):2667–2672.

Epstein-Barr virus (EBV) is an important human pathogen, related to herpes simplex virus (HSV). Elliot Kieff, *Virology*, Third Edition, Edited by B. N. Fields, D. M. Knipe, P. M. Howley, et al. Epstein-Barr Virus and Its Replication. Chapter 74. Pp 2343–2396 and Alan B. Rickinson and Elliot Kieff, Ibid. Chapter 75, pp. 2397–2446. EBV is a lymphotrophic member of the genus Lumphocryptovirus, and belongs to the sub-family gamma-herpesvirinae. Another new member of human virus also belonging to this family is Kaposi's sarcoma-associated herpes virus (KSHV/HHV8). Chang, et al., *Science*, 266:1865–1869 (1994); Cesarman, et al., *N. Eng. J. Med.*, 332:1186–1191 (1995); Soulier, et al., *Blood*, 86:1276–1280 (1995). There are two sub-types of EBV identified and their genomes are nearly identical, but there is no clear relationship between EBV associated diseases and EBV sub-types. Abdul-Hamid, et al., *Virology*, 190: 168–175 (1992) and Sample, et al., *J. Virol.*, 64:4084–4092 (1990). The lytic EBV genome is a linear, double-stranded, 172 Kbp DNA composed of 60 mol % guanine and cytosine. The genome has been sequenced and it was found to be capable of encoding a number of virus specified proteins, which include several enzymes involved in virus DNA synthesis during lytic infection of EBV. In vitro, EBV infection is generally limited to B-lymphocytes, although epithelial cells can also be infected. Sixbey, et al., Nature, 306:480–483 (1983). In humans, the virus genome can be detected in B-lymphocytes and T-lymphocytes as well as epithelial cells. The EBV genome replicates lytically in the linear form and can also be latent as supercoiled circular DNA. The expression of the EBV genome in lytic infected cells is very different from latent infected cells. EBV specified DNA plymerase, Dnase and dThd kinase are only expressed in cells upon lytic DNA replication. Cell culture studies indicated the essential role of EBV specified DNA polymerase for EBV DNA replication during lytic infection, but not for the maintenance of supercoiled EBV DNA in latent infected cells. A unique set of EBV proteins including EBVNA 1 and sometimes, EBNA LP, 2, 3A, 3B, 3C, LMP 1 as well as LMP2 is expressed in latent infected or transformed cells. Elliot Kieff, Virology, Third Edition, Edited by B. N. Fields, D. M. Knipe, P. M. Howley, et al. Epstein-Barr Virus and Its Replication. Chapter 74. Pp 2343–2396 and Alan B. Rickinson and Elliot Kieff, Ibid. Chapter 75, pp. H2397–2446.

Structurally, EBV is similar to that of other herpes viruses- it has a double-stranded DNA genome contained within a nucleocapsid, which is surrounded by a lipid envelope containing viral glycoproteins. A tegument protein occupies the space between the envelope and the nucleocapsid.

While primary EBV infection in infancy appears to be almost asymptomatic, a proportion (in some studies up to 50%) of serologically confirmed primary infections in adolescence or early adult life are manifested as infectious mononucleosis (IM) also called the "Kissing Disease". Transmission of EBV is primarily through the saliva, although some infections are transmitted via blood transfusions. A high percentage (>85%) of patients in the acute phase of infectious mononucleosis secrete EBV. In the mid-1970's, EBV was identified to cause fatal IM/X-linked lymphoproliferative syndrome (XLP) in young male children who had X-linked immunodeficiency. Sullivan and Wood, (Immunodeficiency Rev., 1:325–347 (1989). Fatal EBV infection is also found to be associated with nonfamilial monophagocytic syndrome (VAHS) for which there is no effective therapy. Alan B. Rickinson and Elliot Kieff, Virology, Third Edition, Edited by B. N. Fields, D. M. Knipe, P. M. Howley, et al. Epstein-Barr Virus and Its Replication, Chapter 75, pp. 2397–2446 and Craig, et al., Am. J. Clin. Path., 97:189–194 (1992).

Epstein-Barr virus is also recognized as a causative agent of B-cell proliferative diseases, and is linked to a variety of disease states, including a rare progressive mononucleosis-like syndrome and oral hair leukoplakia in AIDS patients. EBV has also been associated with certain types of cancer such as Burkitt's lymphoma, nasopharyngeal carcinoma, Hodgkin's disease, EBV-associated T-cell lymphoma and nasal T-cell lymphoma. Certain patients, in particular, those with suppressed immune systems such as AIDS patients and organ transplant patients who are being treated with immunosuppressive agents, are particularly susceptible to EBV manifestations, especially the development of EBV-associated lymphomas.

Chu, et al., in PCT application PCT/US95/01253, describe a number of L-nucleoside analogs for use in the treatment of Hepatitis B virus and Epstein-Barr virus infections. One agent disclosed in the PCT application, 2'-fluoro-5-methyl-β-L-arabinofuranosyluridine (L-FMAU), showed good activity against EBV. Noteworthy is the fact that when a 5-methyl group of L-FMAU was substituted with a bromo group, the anti-EBV activity decreased.

Several compounds have been shown to have activity against EBV replication in culture at concentrations non-toxic to cell growth. These include acyclovir (ACV), ganciclovir (DHPG), pencyclovir, D-FMAU and its analogs, 5-bromovinyl dUrd, phosphonoformate and phosphorothioate oligonucleotides. See Lin, et al., Antimicrob. Agents and Chemo. (February) 32(2):265–267 (1988); Lin, et al., Antimicrob. Agents and Chemo., 32(7):1068–1072 (1988); Cheng, et al., Proc. Natl. Acad. Sci. USA, 80:2767–2770 (1983); Datta, et al., Proc. Natl., Acad. Sci. USA, 77:5163–5166 (1980); Datta, et al., Virology, 114:52–59 (1981); Lin, et al., Antimicrob. Agents and Chemo., 31:1431–1433 (1987); Olka and Calendar, Virology, 104:219–223 (1980); Lin, et al., J. Virol., 50:50–55 (1984); Yao, et al., Antimicrob. Agents and Chemo., 37:1420–1425 (1993) and Yao, et al., Biochem. Pharm., (51):941–947 (1966).

PCT application PCT/US97/20647 (WO 98/20879) describes the use of a number of 5-substituted β-L-OddU analogues for the treatment of EBV, VZV and HV-8. The 5-Bromo and 5-Iodo compounds disclosed as being the most active in the series of compounds presented.

Objects of the Invention

It is an object of the present invention to provide compounds, pharmaceutical compositions and methods of treating and/or preventing infections from Epstein Barr virus (EBV), Varicella-Zoster virus (VZV) and Kaposi's Sarcoma Virus (HV-8) and related conditions and/or disease states in patients.

It is an additional object of the present invention to provide, in certain embodiments a method of increasing the retention or metabolic/catabolic half-life of 5-Fluorouracil in cancer patients.

BRIEF DESCRIPTION OF THE FIGURES

FIG. 2 represents the chemical scheme for the synthesis of L-FBVAU and L-FBVRU as described in the examples section of the present specification.

FIG. 3 represents the chemical scheme for the synthesis of 5-BV-SddU as described in the examples section of the present specification.

FIG. 4 represents the chemical scheme for the synthesis of D-5-BV-OddU as described in the examples section of the present specification.

FIG. 5 represents the chemical scheme for the synthesis of 5-Substituted L-Dioxolanyl Uracil Analogues as described in the examples section of the present specification.

BRIEF DESCRIPTION OF THE INVENTION

Figure 1:
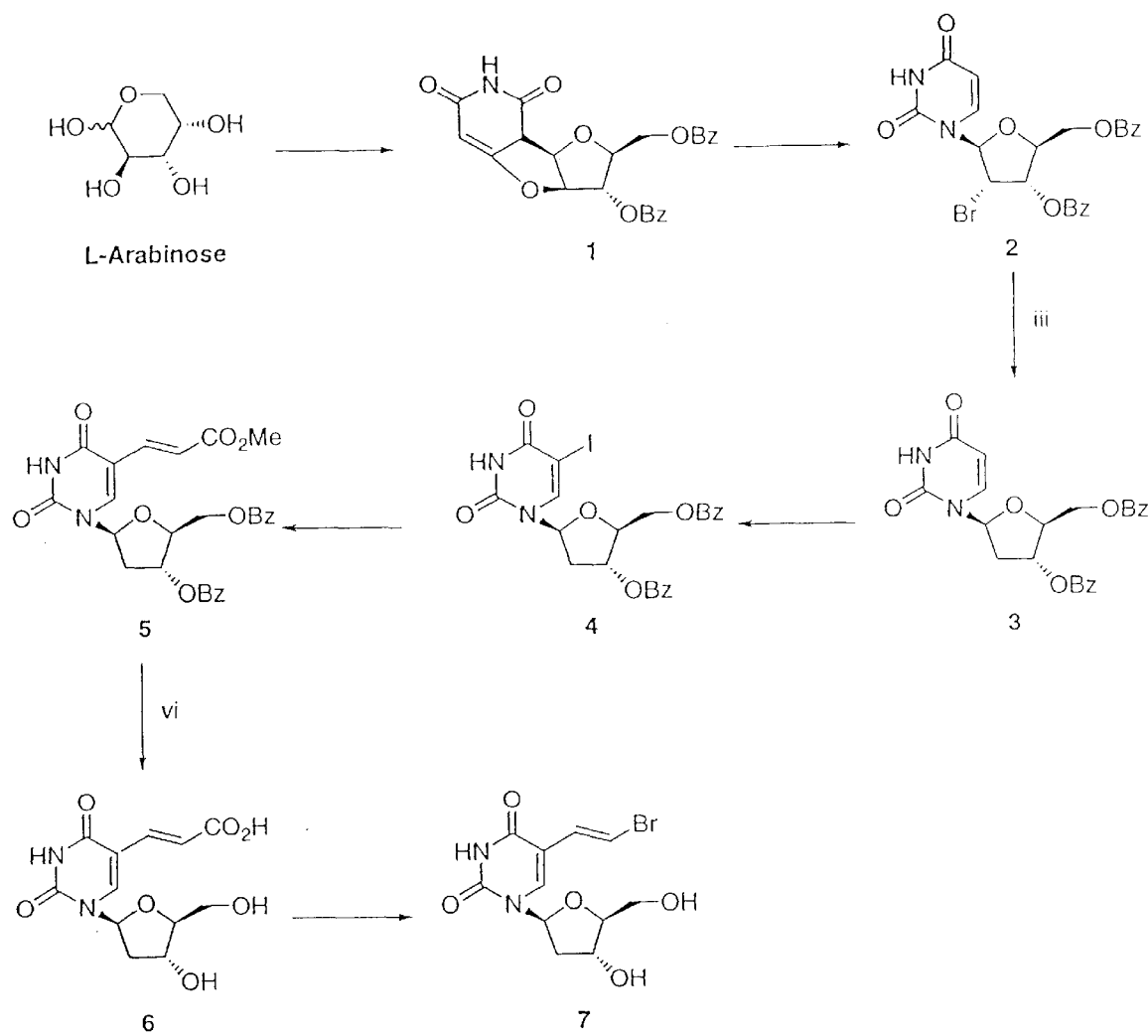
FIG. 1 represents the chemical scheme for the synthesis of L-BDVU as described in the examples section of the present specification.

The present invention relates to the discovery that certain β-L-nucleoside analogs, preferably those analogs containing a 5-halovinyl moiety on the uracil base exhibit unexpectedly high activity against Epstein Barr Virus (EBV), Varicella-Zoster virus (VZV) and Kaposi's Sarcoma Virus (HV-8). In particular, the compounds according to the present invention show potent inhibition of the replication of the virus (viral growth) in combination with very low toxicity to the host cells (i.e., animal or human tissue).

Compounds according to the present invention exhibit primary utility as agents for inhibiting the growth or replication of VZV, EBV and HV-8. Certain of these agents are also useful for inhibiting the growth or replication of other viruses (for example, HSV) or for treating other viral infections and/or related disease states. Other agents may be used as biological probes for testing purposes or as intermediates in the synthesis of related nucleoside compounds having pharmacological activity or for treating cancer and other disease states.

Compounds of the present invention find particular use in combating viral infections which afflict animals, and in particular, humans suffering from Epstein Barr virus, Varicella-Zoster virus or Kaposi's Sarcoma virus (HV-8) infections and their complications. Compounds according to the present invention offer great potential as therapeutic agents against a disease state (in particular, Varicella-Zoster virus) for which there presently are few real therapeutic options. The compounds according to the present invention may be used alone or in combination with agents or other therapeutic treatments.

The compounds according to the present invention are 5-substituted dioxalone uridine nucleoside analogs which have a β-L-configuration. Preferably, in each case, the uracil base is substituted at the 5 position with a trans-substituted chlorovinyl, bromovinyl or iodovinyl, with a substitution at the 5 position of the uracil base with bromovinyl being particularly preferred.

The present invention also relates to methods for inhibiting the growth or replication of Epstein Barr virus, Varicella-Zoster virus or Kaposi's Sarcoma virus comprising exposing the virus to an inhibitory effective amount or concentration of at least one of the disclosed nucleoside analogs. This method may be used in comparison tests such as assays for determining the activities of related anti-VZV, anti-EBV or anti-HV-8 compounds as well for determining the susceptibility of a patient's VZV infection to one of the compounds according to the present invention. The present compounds are preferably used to treat or prevent VZV infections in humans.

The therapeutic aspect according to the present invention relates to methods for treating or preventing VZV, EBV or HV-8 infections in patients, preferably, human patients, comprising administering anti-viral effective amounts of one or more of the compounds according to the present invention to inhibit the growth or replication of the virus in the animal or human patient being treated. In a preferred method aspect according to the present invention, the present compositions are used to prevent or delay the onset of VZV, EBV or HV-8 infections or related conditions or viral complications in a patient, including those patients who have had a blood transfusion and those patients who are immunodeficient or immunocompromised, for example, AIDS patients and transplant patients, among others.

Pharmaceutical compositions based upon these novel chemical compounds comprise one or more of the above-described compounds in a therapeutically effective amount for treating a viral, generally, a VZV, EBV or HV-8 infection, optionally in combination with a pharmaceutically acceptable additive, carrier or excipient.

The compounds according to the present invention, in pharmaceutical dosage form, also may be used as prophylactic agents for inhibiting the growth or replication of VZV, EBV or HV-8. These may be particularly appropriate as anti-VZV, anti-EBV or anti-HV-8 agents. In certain pharmaceutical dosage forms, the pro-drug form, for example, an acylated nucleoside or a nucleoside containing a phosphate ester may be preferred.

While not being limited by way of theory, it is believed that the compounds according to the present invention may induce their inhibitory effect on the growth or replication of VZV, EBV or HV-8 by inhibiting viral DNA synthesis into the viral DNA which causes chain termination. It is unexpected that the present compounds evidence exceptional anti-VZV, anti-EBV and/or anti-HV-8 activity.

In another aspect of the present invention, it has unexpectedly been discovered that the co-administration of one or more compounds according to the present invention along with 5-fluorouracil (FU) in the treatment of cancer and tumors will unexpectedly enhance or increase the retention or metabolic/catabolic half-life of FU and related prodrugs by at least a third, and in certain instances will increase the metabolic/catabolic half-life of FU by a factor of at least 2. This is an unexpected result. Consequently, in this aspect of the present invention in the treatment of cancer and tumors, the administration of FU in the treatment of cancer can be reduced (in both frequency and/or the amount adminstered) through the co-administration of at least one compound according to the present invention and preferably L-β-5(E)-BVOddU.

The compounds according to the present invention are produced by synthetic methods which are readily known to those of ordinary skill in the art and include various chemical synthetic methods which are presented in detail hereinbelow.

DETAILED DESCRIPTION OF THE INVENTION

The following definitions will be used throughout the specification to describe the present invention.

The term "patient" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

The term "Varicella-Zoster virus" (VZV) is used to describe *Herpesvirus varicellae*, also known as chicken pox or herpes zoster. VZV is a herpes virus and is morphologically identical to Herpes Simplex virus, that causes varicella (chicken pox) and herpes zoster in humans. Varicella result from a primary infection with the virus; herpes zoster results from secondary invasion by the same or by reactivation of infection which in many instances may have been latent for a number of years.

The term "Epstein Barr virus" or (EBV) is used throughout the specification to describe the herpes virus found in cell cultures of Burkitt's lymphoma. Structurally, EBV is similar to that of other herpes viruses- it has a double-stranded DNA genome contained within a nucleocapsid, which is surrounded by a lipid envelope containing viral glycoproteins. A tegument protein occupies the space between the envelope and the nucleocapsid. EBV is the causative agent in infectious mononucleosis. Epstein-Barr virus is also recognized as a causative agent of B-cell proliferative diseases, lymphoproliferative syndrome, non-familial monophagocytic syndrome and is linked to a variety of disease states, including a rare progressive mononucleosis-like syndrome and oral hair leukoplakia in AIDS patients. EBV has also been associated with certain types of cancer such as Burkitt's lymphoma, nasopharyngeal carcinoma, Hodgkin's disease, EBV-associated T-cell lymphoma and nasal T-cell lymphoma. Certain patients, in particular, those with suppressed immune systems such as AIDS patients and organ transplant patients who are being treated with immunosuppressive agents, are particularly susceptible to EBV manifestations, especially the development of EBV-associated lymphomas.

The term "Herpes Virus 8" or HV-8 is used throughout the specification to describe a herpes virus which is believed to be the causative agent of Kaposi's sarcoma in AIDS patients. HV-8 and HHV-8 (Human Herpes Virus 8) are one and the same virus.

The term "pharmaceutically acceptable derivative" is used throughout the specification to describe any pharmaceutically acceptable salt or prodrug form (such as an ester, phosphate ester or salt of an ester) of a nucleoside compound which, upon administration to a patient, provides directly or indirectly the nucleoside compound or an active metabolite of the nucleoside compound. In general, the free nucleoside form or acyl prodrug forms of the present compounds, because of the presence of a uracil base, does not readily form salts. However, the mono-, di- and tri-phosphate forms of the nucleoside compounds according to the present invention will form salts on the phosphate moiety. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art.

The term "acyl" is used throughout the specification to describe a group at the 5' position of the nucleoside analog (i.e., at the free hydroxyl position in the dioxolanyl moiety) which contains a $C_1$ to $C_{20}$ linear, branched or cyclic alkyl chain. The acyl group at the 5' position, in combination with the 5' hydroxyl group results in an ester, which, after administration, may be cleaved to produce the free nucleoside form of the present invention. Acyl groups according to the present invention are represented by the structure:

where $R^2$ is a $C_1$ to $C_{20}$ linear, branched or cyclic alkyl chain, alkoxyalkyl, aryloxyalkyl, such as phenoxymethyl, aryl, alkoxy, among others. Preferred acyl groups are those where $R^2$ is $C_1$ to $C_3$. Acyl groups according to the present invention also include, for example, those acyl groups derived from benzoic acid and related acids, 3-chlorobenzoic acid, succinic, capric and caproic, lauric, myristic, palmitic, stearic and oleic, among numerous others including mesylate groups. One of ordinary skill in the art will recognize the acyl groups which will have utility in the present invention, either to synthesize the target pharmaceutical compounds or as prodrug of the nucleosides according to the present invention.

The term "phosphate ester" or "phosphodiester" is used throughout the specification to describe mono-phosphate groups at the 5' position of the dioxanyl moiety or sugar synthon which are diesterified such that the phosphate group is rendered neutral, i.e., has a neutral charge. Phosphate esters for use in the present invention include those represented by the structures:

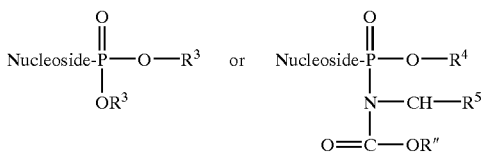

where $R^3$, $R^5$ and $R''$ are selected from a $C_1$ to $C_{20}$ linear, branched or cyclic alkyl group, alkoxyalkyl, aryloxyalkyl, such as phenoxymethyl, aryl and alkoxy, among others, and $R^4$ is a $C_1$ to $C_{20}$ linear, branched or cyclic alkyl or acyl group, alkoxyalkyl, aryloxyalkyl, such as phenoxymethyl, aryl and alkoxy, among others. Preferred monophosphate esters for use in prodrug forms according to the present invention are those where $R^3$ is a $C_1$ to $C_{20}$ is a linear or branched chain alkyl group, more preferably a $C_1$ to $C_3$ alkyl group.

The term "inhibitory effective concentration" or "inhibitory effective amount" is used throughout the specification to describe concentrations or amounts of compounds according to the present invention which substantially or significantly inhibit the growth or replication to of susceptible viruses, especially including EBV, VZV and HV-8.

The term "therapeutic effective amount" or "therapeutically effective amount" is used throughout the specification to describe concentrations or amounts of compounds according to the present invention which are therapeutically effective in treating EBV,VZV and HV-8 infections in humans.

The term "preventing effective amount" is used throughout the specification to describe concentrations or amounts of compounds according to the present invention which are prophylactically effective in preventing or delaying the onset of EBV, VZV and HV-8 infections or related conditions (especially EBV-associated cancer or lymphoma and Kaposi's Sarcoma) in humans.

The term "effective amount" shall mean an amount or concentration of a compound according to the present invention which is effective within the context of its administration.

The term "L-configuration" is used throughout the specification to describe the chemical configuration of the dioxolane uridine nucleoside compounds according to the present invention which is the unnatural configuration. The L-configuration of the sugar moiety of compounds of the present invention contrasts in most instances with the D-configuration of ribose sugar moieties of most naturally occurring nucleosides such as cytidine, adenosine, thymidine, guanosine and uridine. The term "D-configuration" refers to the natural configuration of sugar moeties of the naturally occurring nucleosides.

The term "enantionmerically enriched" is used throughout the specification to describe a nucleoside which includes at least about 95%, preferably at least about 96%, more preferably at least about 97%, even more preferably, at least about 98%, and even more preferably at least about 99% or more of a single enantiomer of that nucleoside. When an L-nucleoside is referred to in this specification, it is presumed that the nucleoside is an enantiomerically enriched nucleoside, unless otherwise stated.

The term "half-life" is used to describe the time that an active agent is found in the bloodstream of a patient before half the concentration of active agent is removed either through metabolism or catabolism. In the present invention, the half-life of 5-fluorouracil (FU) will be increased by at least one third and in certain instances by at least a factor of two (ie., an increase of at least about 100% or a doubling of the half-life) through the co-administration of effective amounts of at least one compound according to the present invention, and in particular, L-β-5(E)BVOddU. The half-life of FU in humans is approximately 25 minutes (generally ranging from about 20–30 minutes although variation outside of this range may be found). The term "retention" refers to the fact that FU will be retained in the bloodstream in a patient for a longer period of time during the co-administration of FU with one or more compound according to the present invention. The term "prodrug" of 5-Fluorouracil is used to describe compounds which function as prodrugs of 5-Fluorouracil and include such compounds as 2-(1)tetrahydrofurano-5-Fluorouracil (I) and 5-Fluoropyrimidin-2-one (II) below.

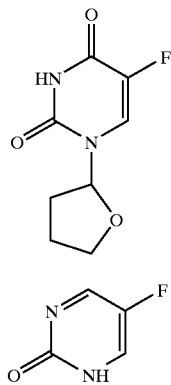

I

II

The present invention, therefore relates to a group of compounds according to the structure:

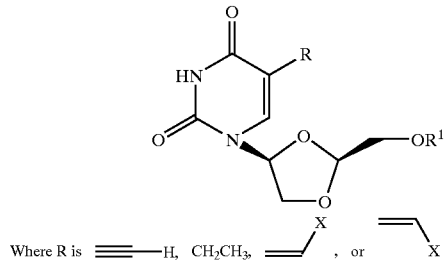

Where R is ≡—H, CH$_2$CH$_3$, , or

X is H, F, Br, Cl, I or CH$_3$ and

R$^1$ is H, a C$_1$ to C$_{20}$ acyl or ether group, a phosphate, diphosphate, triphosphate or phosphodiester group.

In this aspect of the present invention, R is a preferably a trans-substituted vinyl group:

where X is preferably Br or I, most preferably Br.

The present invention also relates to a method for inhibiting the growth or replication of Varicella-Zoster virus (VZV), Epstin Barr virus (EBV) or Kaposi's Sarcoma virus (HV-8) comprising exposing the virus to an inhibitory effective concentration of a compound according to the structure:

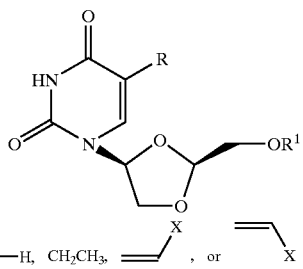

Where R is ≡—H, CH$_2$CH$_3$, , or

X is H, F, Br, Cl, I or CH$_3$ and
R$^1$ is H, a C$_1$ to C$_{20}$ acyl or ether group, a phosphate, diphosphate, triphosphate or phosphodiester group.

In this method aspect of the present invention, R is preferably a trans-substituted vinyl group:

and X is preferably Br or I, most preferably Br.

The present invention is also directed to a method for treating a patient suffering from an infection caused by the Varicella-Zoster virus, Epstein Barr virus or Kaposi's Sarcoma virus comprising administering to said patient a therapeutically effective concentration or amount of a compound according to the structure:

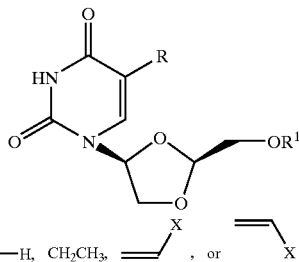

Where R is ≡—H, CH$_2$CH$_3$, , or

X is H, F, Br, Cl, I or CH$_3$ and
R$^1$ is H, a C$_1$ to C$_{20}$ acyl or ether group, a phosphate, diphosphate, triphosphate or phosphodiester group.

In this method aspect of the present invention, R is preferably a trans-substituted vinyl group:

and X is preferably Br or I, most preferably Br.

The compounds according to the present invention are primarily useful for their anti-viral activity, especially their anti-VZV, anti-EBV and anti-HV-8 activity. The present compounds may also be useful for other anti-viral activity. In addition, these compositions may also find use as intermediates in the chemical synthesis of other nucleoside or nucleotide analogs which are, in turn, useful as therapeutic agents or for other purposes, including their use markers in biological tests or as biological probes. Preferably, these compounds find use as novel anti-EBV, anti-VZV or anti-HV-8 agents.

In general, the most preferred anti-viral compounds according to the present invention include those which are less cytotoxic to the host cells and more active to the targeted virus. Certain of the compounds, in pharmaceutical dosage form, may be used as prophylactic agents. These may be particularly appropriate as anti-EBV, anti-VZV or anti-HV-8 agents. Because of their very low toxicity to the patient and excellent anti-viral activity, β-L-5-(E)Bromovinyl-OddU and β-L-5-(E)Iodovinyl-OddU are especially effective anti-prophylactic compounds for treating and/or preventing EBV, VZV and HV-8 infections.

The compounds according to the present invention, because of their low toxicity to host cells, may advantageously be employed prophylactically to prevent EBV, VZV or HV-8 infection or to prevent the occurrence of clinical symptoms associated with the viral infection. Thus, the present invention also encompasses methods for the prophylactic treatment of viral infections, and in particular EBV, VZV and HV-8 infections. In this aspect according to the present invention, the present compositions are used to prevent or delay the onset of an EBV, VZV or HV-8 infection infection or EBV-, VZV- or HV-8 or related diseases such as lymphoma or cancer, including Kaposi's Sarcoma in patients, including those patients who have had a blood transfusion and those patients who are immunodeficient or immunocompromised, for example, AIDS patients and transplant patients, among others.

This prophylactic method comprises administering to a patient in need of such treatment or who is at risk for the devolopment of EBV-, VZV- or HV-8-related symptoms or diseases an amount of a compound according to the present invention effective for alleviating, preventing or delaying the onset of the the viral infection.

In a further aspect of the present invention, an anti-cancer method is provided for increasing the retention of 5-Fluorouracil (FU) in a patient, said method comprising co-administering with FU an amount of at least one compound according to the present invention effective to substantially enhance the retention of FU and/or one or more of its active metabolites. It is an unexpected result that the retention of FU is at least a third greater when co-administered with one or more of the compounds according to the present invention as compared to the administration of FU alone. In certain aspects, the retention of FU from co-administration with a compound according to the present invention may be at least twice that expected from administration of FU alone, thus reducing the frequency and/or the amount of 5FU administered to the cancer patient. This is an unexpected result and a significant advantage over the prior art method.

The compounds according to the present invention are produced by synthetic methods which are readily known to those of ordinary skill in the art and include various chemical synthetic methods as elaborated in significantly more detail in the Examples which follow. In general, compounds according to the present invention are synthesized by condensing a previously synthesized nucleoside base onto the appropriate dioxolanyl or oxathiolanyl synthon which will ultimately give rise to a nucleoside analog having the desired L-configuration. In certain instances, the synthetic pathway may deviate from the general synthetic pathway for a specific nucleoside analog. Other compounds, for example deoxyribonucleosides, may be synthesized by condensing an appropriate 5-substituted uracil derivative onto L-arabinose, and then reducing a bromo or other group at the 2' position of the sugar to form the β-L-deoxynucleoside analog.

During chemical synthesis of the various compositions according to the present invention, one of ordinary skill in the art will be able to practice the present invention without undue experimentation. In particular, one of ordinary skill in the art will recognize the various steps that should be performed to introduce a particular substituent at the desired position of the base or a substituent at the desired position on the sugar moiety. In addition, chemical steps which are taken to "protect" functional groups such as hydroxyl or amino groups, among others, as well as "de-protect" these same functional groups, will be recognized as appropriate within the circumstances of the syntheses. A large number of protecting groups may be used in the present invention. In the case of the introduction of any one or more acyl groups onto the 5' position (or the uracil base) of the nucleoside, standard techniques, well known by those of ordinary skill, may be used. Synthesis of the 5'-mono, di-or triphosphates, or diesters of phosphates (as neutral prodrug forms), may also be synthesized by well-known methods in the art.

In general, synthesis of the compounds according to the present invention proceeds by first synthesizing the appropriate dioxolanyl or oxathiolanyl synthon and then condensing the substituted base onto the dioxolanyl synthon. An appropriate synthetic approach for synthesizing the present invention may be found in attached schemes 1–4 and as is generally described in the examples. Various equivalent synthetic approaches may also be used in the synthesizing the present compounds. The specific synthesis of the compounds according to the present invention is presented below.

Chemistry. The synthesis of 5-(E)-bromovinyl-2'-deoxy-β-L-uridine (L-BVDU) was accomplished via 5-iodo-2'-deoxy-L-uridine from L-arabinose based on Holy's method (Holy, A. 2'-Deoxy-L-uridine. Total synthesis of a uracil 2'-deoxynucleoside from a sugar 2-aminooxazoline through a 2,2'-anhydronucleoside intermediate. In *Nucleic Acid Chemistry, Improved and New Synthetic Procedures, Methods and Techniques*, Part 1; L. B. Townsend and R. S. Tipson, Eds.; Wiley, 1978, pp 347–353) and the Heck reaction (Dyer, R. L. E-5-(2-Bromovinyl)-2'-deoxyuridine. The synthesis of E-5-(2-bromovinyl)-2'-deoxyuridine from 2'-deoxy-5-iodouridine. In *Nucleic Acid Chemistry, improved and New Synthetic Procedures, Methods and Techniques*, Part 4; L. B. Townsend and R. S. Tipson, Eds.; Wiley, 1978, pp 79–83.) with minor modifications as shown in Scheme 1 (FIG. 1).

3',5'-Di-O-benzoyl-2,2'-anhydro-L-uridine (1) obtained from L-arabinose in 3 steps was transformed into the 2'-bromo-2'-deoxyuridine derivative 2 by heating with acetyl bromide in acetonitrile in 81% yield. The reductive dehalogenation of the 2'-bromo derivative 3 afforded protected L-2'-deoxyuridine 3, which gave the 5-iodouracil analog 4 in treatment with iodine and $HNO_3$ in refluxing dioxane in 77% yield from 2. Coupling of compound 4 with methyl acrylate in dioxane was catalyzed by triphenylphosphine and palladium acetate. The resulting product 5 (77%) was subjected to saponification with NaOH followed by acidification with HCl to give free acid 6 in 88% yield. Treatment of compound 6 with N-bromosuccinimide (NBS) and potassium carbonate in DMF provided the desired product 7 (67%).

2'-deoxy-2'-fluoro-β-L-arabinofuranosyl nucleoside was also prepared by using a similar procedure mentioned for the synthesis of L-BVDU via L-FIAU, which was prepared from L-arabinose according to the procedure reported by our group. See Du, et al., "Practical synthesis of L-F M A U from L-arabinose." in *Nucleosides Nucleotides* 1999 Thus, the free 5-iodouracil derivative 8 was treated with methyl acrylate in the presence of $Pd(OAc)_2$ and $Ph_3P$ in dioxane. Saponification with NaOH followed by acidification with HCl gave 10, which was decarboxylated in DMF in the presence of N-bromosuccinimide and $K_2CO_3$ to give 11

(Scheme 2). Several routes for the syntheses of 2'-deoxy-2'-fluoro-β-D-ribonucleosides have been developed so far, including opening 2,2'-anhydronucleosides with a fluorinating agents such as HF/dioxane (Codington, et al., *J. Org. Chem.* 1964, 29, 558–564) or KF/crown ether (Mengel, et al., *Anzew. Chem. Int. Ed. Engl.* 1978, 17, 525), the coupling of a suitably blocked 2-deoxy-2-fluorofibofuranoside with a nucleobase (Mikhailopulo, et al., *Carbohydr. Res.* 1995, 278, 71–89) the enzyme catalyzed transglycosylation (Tuttle, J. J. Med. Chem. 1993, 36, 119–123. 163) nucleophilic displacement of the 2'-O-trifluoromethanesufonyl arabinonucleosides by tetra-n-butylammonium fluoride (TBAF)(See, Ikehara, et al., *Chem. Pharm. Bull.* 1981, 29, 1034–1038) and the direct introduction of the fluorine atom by diethylaminosulfur fluoride (DAST) to an arabinonucleoside (Hayakawa, et al. *Chem. Phar. Bull.* 1990, 38, 1136–1139). This last methodology was adopted for the synthesis of pyrimidine 2'-deoxy-2'-fluoro-L-ribofuranosyl nucleoside (Scheme 2) because reliable yield can be achieved on a relatively large scale. Thus, 2,2'-anhydro-L-urine was prepared from L-arabinose in two steps according to a literature procedure (Holy, A. 2'-Deoxy-L-uridine. Total synthesis of a uracil 2'-deoxynucleoside from a sugar 2-aminooxazoline through a 2,2'-anhydronucleoside intermediate. In *Nucleic Acid Chemistry, Improved and New Synthetic Procedures, Methods and Techniques*, Part 1; L. B. Townsend and R. S. Tipson, Eds.; Wiley, 1978, pp 347–353) and then treated 3,4-dihydropyran in DMF followed by saponification to give 12 in a 40% total yield. 12 was then treated successively with DAST, p-TsOH, and $Ac_2O$ in pyridine to give the key intermediate 13 in a 41% total yield after crystallization from EtOH. Treatment of 13 with IC1 in refluxing $CH_2Cl_2$ (Robins, et al., *J. Org. Chem.* 1983, 48, 1854–1862) followed by ammonolysis with sat. $NH_3$/MeOH afforded the 5-iodouracil analog 14, which was treated with methyl acrylate in the presence of $Pd(OAc)_2$ gave 15 in a 76% yield, from which the 5-E-bromovinyluracil analog 17 was obtained in a 36% total yield (FIG. 2, Scheme 2).

The synthesis of oxathiolane and dioxolane derivatives was accomplished by coupling methods reported by Jin et al. (Jin, et al., *J. Org. Chem.* 1995, 60, 2621–2623). Oxathiolane sugar moieties were prepared from dithiane-1,4-diol (Jin, et al., *J. Org. Chem.* 1995, 60, 2621–2623) and dioxolane sugar moieties prepared from D-mannose (Kim, *J. Med. Chem.* 1992, 35, 1987–1995) and L-gulonic g-lactone (Kim, et al., *J. Med. Chem*, 1993, 36, 519–528), respectively, with minor modifications. The (halovinyl)uracils were prepared according to the methods of Jones et al. (Jones, et al., *Tetrahedron Lett*, 1979, 4415). By condensation of 5-formyluracil with malonic acid, followed by halosuccimide treatment. Subjection of the ester chloride 18 to reaction with persilylated 5-E-bromovinyluracil in $CH_2Cl_2$ in the presence of TMSI afforded the expected cis nucleoside as a major (cis:trans, 30:1 by $^1$H NMR) in 87% yield. Reduction of compound 19 with $NaBH_4$ in EtOH provided 20 in 70% yield. It is of note that although $NaBH_4$ reduction of ester is known to be sluggish, reduction of 19 allowed comparable yield, probably due to a-hydroxy group (Mauger, et al.*J. Chem. Soc., Chem. Commun*. 1986, 395; and Corsano, et al., *J. Chem. Soc., Chem. Commun.* 1971, 1106). Enantiomer 23 was also obtained by condensation of 21 with 5-E-bromovinyluracil followed by reduction (FIG. 3, Scheme 3). Physical data of both enantiomers were well-matched, including optical rotation. Glycosylations of dioxolane sugar moieties with appropriate uracil bases were also performed with TMSI as a coupling promotor. TMSI-mediated coupling of a chiral oxathiolane sugar with a protected hydroxymethyl substituent at the 2-position is known to be nonstereoselective (Beach, *J. Org. Chem.* 1992, 57, 2217–2219; and Humber, et al. *Tetrahedron Lett.* 1992, 32, 4625–4628). Interestingly, condensation of 24 using TMSI allowed about 3:1 ratio of β-isomer and α-isomer, which ratio were consistent with different bases in coupling. Deprotection of 25 and 26 with TBAF in $CH_3CN$ provided the free nucleosides 27 and 28 in high yields, respectively (FIG. 4, Scheme 4) (See, Lee, et al.,*J. Med. Chem.* 1999, 42, 1320–1328). The 5-E-halovinyluracil analogs 36–41 possessing dioxolane sugar moiety of L-configuration were also obtained with similar methods to the synthesis of 27 and 28. The E-configurations of the synthesized nucleosides were identified by the coupling constant (13.6 Hz) for the vinyl protons in the $^1$H NMR spectrum and confirmed in comparison with physical data of available D-isomers. 5-Ethyl, 5-vinyl, and 5-acetylene uracil analogs were synthesized from L-5-I-OddU 42 (Lin, et al.,*J. Med. Chem.* 1999, 42, in press) according to Walker and coworkers' methods (See, Rahim, et al, *J. Med. Chem.*, 1996, 39, 789–795). L-5-I-OddU was converted to di-p-toluoyl protected derivative 43, which was further converted to 5-vinyl uracil analogues in the presence of tetravinyltin and tetrakistriphenylphosphine palladium in HMPA at 50° C. Suprisingly, during the coupling reaction, $N^3$-p-Toluoyl group was deprotected to give mono-p-Toluoyl protected nucleoside 44. Thus, deprotection of 44 using sat. $NH_3$/MeOH afforded L-dioxolane 5-vinyl uracil analogue 45 in 70% yield from 43, which was comparable yield compared to the literature yield. Rahim, et al, supra). 5-Acetylene uracil analog 47 was also prepared by coupling the protected 5-iodouracil nucleoside 42 with terminal alkyne (De Clercq, et al., *J. Med. Chem.*, 1983, 26, 661–666). Compound 46 was treated with trimethylsilylacetylene in triethylamine in the presence of bis(triphenylphosphine L palladium (II) chloride and copper (I) iodide. The resulting coupling product was deprotected with methanolic sodium methoxide to afford the desired product 47 in 58% yield. Hydrogenation of 47 with 10% Pd-C in EtOH gave the 5-ethyluracil analog 48 in a quantitative yield.

The therapeutic aspect according to the present invention relates to methods for treating VZV, EBV and HV-8 infections in patients comprising administering anti-viral effective amounts of the compounds according to the present invention to inhibit the growth or replication of the viruses in the patient being treated.

In a preferred method aspect according to the present invention, the present compositions are used to prevent or delay the onset of VZV, EBV or HV-8 infections or related conditions and/or diseases in patients. The method comprises administering to such a patient a prophylactically effective amount (which generally is the same as a therapeutically effective amount) of one or more of the compositions according to the present invention to the patient to delay or prevent a VZV, EBV or HV-8 infection and/or the related condition or disease state.

Pharmaceutical compositions based upon these novel chemical compounds comprise the above-described compounds in a therapeutically effective amount for treating a viral, especially aVZV, an EBV or HV-8 infection, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and ether derivatives, phosphate esters and various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition, in preferred embodiments, an EBV, a VZV or HV-8 infection, especially a VZV infection. In general, a therapeutically effective amount of the present compound in pharmaceutical dosage form usually ranges from about 0.1 mg/kg to about 100 mg/kg or more, more preferably, slightly less than about 1 mg./kg. to about 25 mg./kg. of the patient or considerably more, depending upon the compound used, the condition or infection treated and the route of administration. In the case of VZV, EBV or HV-8 infections, the active compound is preferably administered in amounts ranging from about 0.5 mg/kg to about 25 mg/kg of the patient, depending upon the pharmacokinetics of the agent in the patient. This dosage range generally produces effective blood level concentrations of active compound which may range from about 0.05 to about 100 micrograms/cc of blood in the patient. For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of admnistration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prod-drug forms of the nucleoside compounds according to the present invention.

In particularly preferred embodiments according to the present invention, the compounds and compositions are used to treat, prevent or delay the onset of viral infections of mammals and in particular EBV, VZV and HV-8 infections in humans. In its preferred embodiments, the compounds are used to treat EBV, VZV and HV-8 infections, especially VZV infections in humans. Preferably, to treat, prevent or delay the onset of EBV, VZV and HV-8 infections, the compositions will be administered in oral dosage form in amounts ranging from about 250 micrograms up to about 500 mg or more at least once a day, preferably, up to four times a day. The present compounds are preferably administered orally, but may be administered parenterally, topically or in suppository form.

The compounds according to the present invention, because of their low toxicity to host cells, may advantageously be employed prophylactically to prevent EBV, VZV or HV-8 infection or to prevent the occurrence of clinical symptoms associated with the viral infection. Thus, the present invention also encompasses methods for the prophylactic treatment of viral infections, and in particular EBV, VZV and HV-8 infections. In this aspect according to the present invention, the present compositions are used to prevent or delay the onset of an EBV, VZV or HV-8 infection infection or EBV-, VZV- or HV-8-related diseases such as lymphoma or cancer, including Kaposi's Sarcoma in patients, including those patients who have had a blood transfusion and those patients who are immunodeficient or immunocompromised, for example, AIDS patients and transplant patients, among others. This prophylactic method comprises administering to a patient in need of such treatment or who is at risk for the development of EBV-, VZV- or HV-8-related symptoms or diseases an amount of a compound according to the present invention effective for alleviating, preventing or delaying the onset of the the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of β-L-BVOddU and β-L-BVIOddU and related compounds of this invention for the treatment of VZV, EBV or HV-8 infections, these compounds may be administered within the same dosage range for therapeutic treatment (i.e., about 250 micrograms up to about 500 mg. or more from one to four times per day for an oral dosage form) as a prophylactic agent to prevent the proliferation of EBV, VZV or HV-8 or alternatively, to prolong the onset of an EBV, VZV or HV-8 infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

In a particularly preferred pharmaceutical composition and method for treating VZV, an inhibitory effective amount of β-L-BVOddU or β-L-IVOddU is administered to a patient suffering from such an infection to treat the infection and alleviate the symptoms of such infection.

As indicated, compounds according to the present invention may be administered alone or in combination with other agents, especially including other compounds of the present invention or compounds which are otherwise disclosed as being useful for the treatment of EBV, VZV and HV-8 infections such as those disclosed in PCT/US97/20647 (WO 98/20879), which is incorporated by reference, herein. Other compounds which may be used in combination with those of the present invention include those which are disclosed in U.S. Pat. No. 5,565,438, which is incorporated by reference herein, such as β-L-FMAU and related compounds. Additional compounds which may be combined with compounds according to the present invention for the treatment of VZV, EBV, HV-8 infections and related conditions and diseases include those which are disclosed in any one or more of the following U.S. Patents, all of which are incorporated by reference herein: U.S. Pat. No. 5,885,957; U.S. Pat. No. 5,643,891; U.S. Pat. No. 5,521,163; U.S. Pat. No. 5,356,882; U.S. Pat. No. 5,079,235; U.S. Pat. No. 5,886,013; U.S. Pat. No. 5,840,728; U.S. Pat. No. 5,714,516; U.S. Pat. No. 5,597,824; U.S. Pat. No. 5,424,295; U.S. Pat. No. 5,216,142; U.S. Pat. No. 5,079,235; U.S. Pat. No. 5,055,458; U.S. Pat. No. 5,036,072; U.S. Pat. No. 5,036,071; U.S. Pat. No. 5,028,596; U.S. Pat. No. 4,287,188; U.S. Pat. No. 4,863,906; U.S. Pat. No. 4,777,166; U.S. Pat. No. 4,714,701; U.S. Pat. No. 4,652,580; U.S. Pat. No. 4,596,798; U.S. Pat. No. 4,963,555; U.S. Pat. No. 4,210,638; U.S. Pat. No. 5,683,990; U.S. Pat. No. 5,602,130; U.S. Pat. No. 5,086,044; and U.S. Pat. No. 5,276,020, among others. The compounds disclosed in the above-referenced patents may be used in combination with the present compounds for their additive activity or treatment profile against EBV, VZV and/or HV-8 and in certain instances, for their synergistic effects in combination with compounds of the present invention. Preferred secondary or additional compounds for use with the present compounds are those which do not inhibit EBV, VZV or HV-8 by the same mechanism as those of the present invention. Certain compounds according to the present invention may be effective for enhancing the biological activity of certain agents according to the present invention by reducing the metabolism or inactivation of other compounds and as such, are co-administered for this intended effect.

In a particularly preferred pharmaceutical composition and method aspect of the present invention for treating VZV infections, an inhibitory effective amount of β-L-BVOddU or β-L-IVOddU is administered to a patient suffering from such an infection to treat the infection and alleviate the symptoms of such infection.

While not being limited by way of theory, it is believed that the compounds according to the present invention primarily induce their inhibitory effect on the growth or replication of the virus by functioning to inhibit viral DNA synthesis.

The present invention is now described, purely by way of illustration, in the following examples. It will be understood by one of ordinary skill in the art that these examples are in no way limiting and that variations of detail can be made without departing from the spirit and scope of the present invention.

EXAMPLES

General Methods. Melting points were determined on a Mel-temp II and are uncorrected. $^1$H NMR spectra were recorded on a Bruker 400 AMX spectrometer for 400 MHz, with $Me_4Si$ as internal standard. Chemical shifts (δ) are reported in parts per million (ppm) and signals are reported as s (singglet), d (doublet), t (triplet), q (quartet), m (multiplet), or br s (broad singlet). IR spectra were measured on a Nicolet 510P FT IR spectrometer. Optical rotations were perfomed on a Jasco DIP-370 Digital Polarimeter. TLC were performed on Uniplates (silica gel) purchased from Analtech Co. Column chromatography was performed using either Silica Gel-60 (220–440 mesh) for flash chromatography or Silica Gel G (TLC grade>440 mesh) for vacuum flash column chromatography. UV spectra were obtained on a Beckman DU 650 spectrophotometer. Elemental analysis was performed by Atlantic Microlab, Inc., Norcross, Ga.

3',5'-Di-O-benzoyl-2'-bromo-2'-deoxy-L-uridine (2). To a suspension of 1 (11.00 g, 25.3 mmol) in acetonitrile (220 mL) at 60° C. was added acetyl bromide (6.7 mL, 90.6 mmol). The reaction was continued for 5 h at 60° C., and then solvent was removed under reduced pressure. The residue was recrystallized from methanol to give 2 (10.50 g, 81%) as a white solid: mp 169–170° C.; $[\alpha]_D$+25.2 (c 1.00, $CHCl_3$); UV (MeOH) $\lambda_{max}$ 246 nm; $^1$H NMR ($CDCl_3$) δ 9.32 (s, 1H, NH, $D_2O$ exchangeable), 8.12-(m, 4H, aromatic H), 7.66–7.43 (m, 6H, aromatic H), 7.44 (d, 1H, H-6, J=8.2 Hz), 6.36 (d, 1H, H -1', J=5.4 Hz), 5.61 (dd, 1H, H-5, J=8.2 and 1.7 Hz), 5.52 (app. t, 1H, H-3', J=5.5), 4.84–4.66 (m, 4H, H-2', H-4' and H-5'); Anal Calcd. for $C_{23}H_{19}BrN_2O_7$: C, 53.61; H, 3.71; Br, 15.51; N, 5.44. Found; C 53.49; H. 3.73; Br, 15.58; N, 5.46.

3',5'-Di-O-benzoyl-2'-deoxy-L-uridine (3). To a suspension of 2 (3.00 g, 5.8 mmol) in dry toluene (100 mL) were added n-tributyltin hydride (4.9 mL, 17.5 mmol) and AIBN (200 mg, 1.2 mmol). The reaction mixture was heated at 100° C. and kept stirring for 2 h. Solvent was then removed under reduced pressure to obtain a white solid, which was dissolved in acetonitrile. The solution was washed with hexanes and the hexanes layer was extracted with acetonitrile. Combined acetonitrile layers were concentrated to a white solid (2.54 g, quantitative yield), which was used in the next reaction without further purification: mp 217–218° C.; $^1$H NMR (CDCl$_3$) δ9.00 (s, 1H, NH, D$_2$O exchangeable), 8.09–8.00 (m, 4H, aromatic H), 7.64–7.45 (m, 7H, aromatic H and H-6), 6.41 (dd, H-1', J=8.3, 5.6 Hz), 5.65–5.59 (m, 2H, H-3' and H-5), 4.75 (dd, 1H, H-5', J=12.2 and 3.3 Hz), 4.70 (dd, 1H, H-5", J=12.2 and 3.6 Hz), 4.56 (app. dd, 1H, H-4', J=5.8, 3.0),2.77 (ddd, 1H, H-2'α, J=14.4, 5.6 and 1.7 Hz), 2.33 (ddd, 1H, H-2'β, J=14.4, 8.3 and 6.6 Hz).

3',5'-Di-O-benzoyl-2'-deoxy-5-iodo-L-uridine (4). A mixture of 3 (1.00 g, 2.3 mmol), iodine (1.16 g, 4.6 mmol), dioxane (60 mL) and 1N HNO$_3$ (40 mL) was refluxed for 1h. After evaporation of the solvent, the solid was washed with ether and filtered. The residue was dissolved in chloroform, dried over NaSO$_4$ and concentrated to give 4 as a white solid (1.00 g, 77%): mp 190–191° C.; [α]$_D$+102.6(c 1.00, CHCl$_3$); UV (CHCl$_3$) $\lambda_{max}$ 244.5,282.5 nm; $^1$H NMR (CDCl$_3$) δ 8.97 (s, 1H, N exchangeable), 8.08–8.04 (m, 4H, aromatic H), 7.97 (s, 1H, H-6), 7.64–7.45 (m, 6H, aromatic H), 6.39 (dd, 1H, H-1', J=8.4, 5.5 Hz), 5.64 (d, 1H, H-3', J=6.4 Hz), 4.76 (m, 1H, H-5'), 4.59 (m, 1H, H-4'), 2.80 (dd, 1H, H-2'α, J=14.2, 5.5), 2.32 (ddd, 1H, H-2'β, J=14.2, 8.4 and 6.4 Hz); Anal. Calcd. for C$_{23}$H$_{19}$IN$_2$O$_7$: C, 49.13; H, 3.40; I, 22.57; N, 4.98. Found; C, 48.96; H, 3.38; I, 22.64; N, 5.01.

3',5'-Di-O-benzoyl-E-5-(2-carbomethoxyvinyl)-2'-deoxy-L-uridine (5). To a solution of freshly distilled triethylamine (0.9 mL) in dry dioxane (80 mL) were added triphenylphosphine (115 mg, 0.4 mmol) and palladium (II) acetate (49 mg, 0.2 mmol), and the mixture was refluxed for 10 min. The resulting dark-red-black solution was cooled just below reflux temperature and methyl acrilate (0.8 ml, 8.9 mmol) was added in one portion, immediately followed by dry 4 (2.50 g, 4.4 mmol). After a further portion of triethylamine (0.3 ml) was added, the stirring mixture was gently refluxed for 4 h. The reaction mixture was filtered on a celite pad, washing with methylene chloride; the solvent was removed under reduced pressure to give a brown syrup which was purified by flash chromatography silica gel (hexanes-acetate 1:1) to yield 1.78 g (77%) of 5 as a white solid: mp 171–172° C.; [α]$_D$+104.9(c 0.20, CHCl$_3$); UV (CHCl$_3$) $\lambda_{max}$ 242.0, 300.0 nm; $^1$H NMR (CDCl$_3$) δ 9.96)s, 1 NH, D$_2$O exchangeable), 8.08–8.02 (m, 4H, aromatic H), 7.84 (s, 1H, H-6), 7.64–7.43 (m, 6H, aromatic H), 7.12 (d, 1H, vinylic H, J=15.8 Hz), 6.91 (d, 1H, vinylic H, J=15.8 Hz), 6.39 (dd, 1H, H-1', J=8.4, 5.5 Hz), 5.64 (d, 1H, H-3', J=6.4 Hz), 4.78 (m, 1H, H-5'), 4.61 (m, 1H, H-4'), 3.73 (m, 3H, OCH$_3$), 2.85 (m, 1H, H-2'α), 2.33 (m, 1H, H-2'β); Anal. Calcd. for C$_{27}$H$_{24}$N$_2$O$_9$: C, 62.31; H, 4.65; N, 4.65. Found; C, 62.41; H, 4.74; N, 4.93.

E-5-(2-Carboxyvinyl)-2'-deoxy-L-uridine (6). To a solution of 5 (4.25 g, 8.2 mmol) in THF (25 mL) was added 2M NaOH (25 mL) and the mixture was stirred at rt for 90 min. After tlc indicated loss of starting material, solvent's volume is reduced to half by evaporation under reduced pressure, and the resulting mixture is washed with ether (3×20 mL). The water solution was cooled in an ice bath and brought to pH 2 by addition of concentrated HCl (ca. 5.0 mL). The precipitated solid was filtered, washed with water and acetone and dried to yield 2.15 g (88%) of 6 as a white solid: mp 230° C. (dec.); [α]$_D$+2.8 (c 0.20, DMF); UV (MeOH) $\lambda_{max}$ 206.0, 260.0, 300.0 nm; $^1$H NMR δ 12.21 (bs, 1H, COOH, D$_2$O exchangeable), 11.62 (s, 1H, NH, D$_2$O exchangeable), 8.38 (s, 1H, H-6), 7.28 (d, 1H, vinylic H, J=16.0 Hz), 6.76 (d, 1H, vinylic H, J=16.0 Hz), 6.12 (app. t, 1H, H-1', J=6.3 Hz), 5.19 (m, 2H, OH-3' and OH-5', D$_2$O exchangeable), 4.24 (m, 1H, H-3'), 3.78 (m, 1H, H-4'), 3.61 (m, 2H, H-5'), 2.16 (m, 2H, H-2'); Anal. Calcd. for C$_{12}$H$_{14}$N$_2$O$_7$.0.25H$_2$O: C, 47.61; H, 4.82; N, 9.25. Found; C, 47.73; H, 4.98; N, 9.19.

E-5-(2-Bromovinyl)-2'-deoxy-L-uridine (7). To a solution of 6 (200 mg, 0.67 mmol) in DMF ( mL) was added potassium carbonate (190 mg, 1.48 mmol) and the suspension was stirred at rt for 15 min. A solution of N-bromosuccinimide (130 mg, 0.73 mmol) in DMF (I mL) was added dropwise over min). The resulting suspension was immediately filtered under suction and the solid was thoroughly washed with DMF. The combined filtrate and washings were evaporated to dryness in vacuo to remove completely DMF and the residue was purified by flash-chromatography on silica gel (methanol-chloroform 1:10) to yield 150 mg (67%) of 7 as a white solid: mp 156° C. (dec.); [α]$_D$–19.4(c 0.20, MeOH); UV (MeOH) $\lambda_{max}$ 245.0 nm (ε 1889) (pH 2), 243 nm (ε 2145) (pH 7), 253.5 nm (ε 2079) (pH 11

E-5-(2-Methoxycarbonylvinyl)-(2-deoxy-2-fluoro-β-L-arabinofuranosyl) uracil (9). A mixture of Ph$_3$P (40 mg, 0.15 mmol), Pd(OAc)2 (20 mg, 0.08 mmol), and Et$_3$N (0.4 mL, 2.8 mmol) in 1, dioxane (15 mL) was refluxed to form a dark-red solution and then cooled to just below reflux. To this, methyl acrylate (0.36 mL, 4.0 mmol) was added, followed by 8 (300 mg, 0.8 mmol) with dioxane (10 mL) and Et$_3$N (0.15 mL). The mixture was refluxed for 0.5 h and then filtered through a Celite pad, washed with dioxane. The combined filtrate was evaporated to dryness and purified on a silica gel column (9:1 CHCl$_3$:MeOH) to give 9 as a white foam (145 mg, 54%): UV (MeOH) $\lambda_{max}$ 299.0 nm; $^1$ (DMSO-d$_6$) δ 11.79 (s, 1H, NH, D$_2$O exchangeable), 8.35 (s, 1H, H-6), 7.41 (d, 1H, Ha, J=15.9 Hz), 6.90 (d, 1H, Hb, J=15.8 Hz), 6.14 (dd, 1H, H-1',J$_{1',F}$=14.2 Hz), 5.81 (d, 1H, 3'-OH, D$_2$O exchangeable), 5.25 (t, 1H, D$_2$O exchangeable 5'-OH), 5.10 (dt, J$_{F-H}$=52.6 Hz, 1H, H-2'), 4.26 (dt, J$_{F-H}$=19.8 Hz, 1H, H-3'), 3.84 (m, 1H, H-4'), 3.69 (dm, 2H, H-5'); Anal. Calcd. for C$_{13}$H$_{15}$FN$_2$O$_7$.0.8H$_2$ C, 45.30; H, 4.82; N 8.13. Found; C, 45.55; H, 4.56; N, 8.03.

E-5-(2-Carboxyvinyl)-(2-deoxy-2-fluoro-β-L-arabinofuranosyl) uracil (10). A solution of 9 (135 mg, 0.41 mmol) in a 2 N Na OH solution (5 mL) was stirred at room temperature for 1.5 h, then cooled in an ice bath. It was carefully adjusted to ca. pH 1 with 12 N Hcl and stirred for 10 min. The white precipitate was collected by filtration and washed with water and acetone to give 10 as a white powder (96 mg, 74%): mp 284° C. (dec.); UV (MeOH) $\lambda_{max}$ 298.0, 268.0 nm (sh); $^1$H NMR (DMS 11.80 (s, 1H, NH, D$_2$O exchangeable), 8.28 (s, 1H, H-6), 7.31 (d, 1H, Ha, J=15.8 Hz), 6.79 (d, 1H, Hb, J=15.9 Hz), 6.12 (dd, 1H, H-1', J$_{1',F}$=14.0 Hz), 5.90 (d, 1H, 3'-OH, D$_2$O exchangeable), 5.23 (t, 1H, 5'-OH, D$_2$O exchangeable), 5.08 (dt, 1H, H-2'J$_{F-H}$=52.7 Hz), 4.27 (dt, 1H, H-3', J$_{F-H}$=19.6 Hz), 3.81 (m, 1H, H-4'), 3.65 (dm, 2H, H-5'); Anal. Calcd. for C$_2$H$_3$FN$_2$O.1.6H$_2$O: C, 41.76; H, 4.70; N, 8.12; Found; C, 41.41; H, 4.37; N, 7.93.

E-5-(2-Bromovinyl)-(2-deoxy-2-fluoro-β-L-arabinofuranosyl) uracil (11). A suspension of 10 (80 mg, 0.25 mmol) and KHCO$_3$ (100 mg, 1.0 mmol) in DMF (1.5 mL) was stirred at room temperature for 20 min. To this, N-bromosuccunimide (53 mg, 0.3 mmol) in DMF (1.0 mL) was added. The mixture was stirred at room temperature for 1.5 h then filtered, washed with methanol. The filtrate was evaporated to dryness and purified on preparative TLC (6:1 CHCl$_3$:MeOH). After coevaporation with ether, 11 was obtained as a white foam (47 mg, 53%): mp 190–192 (dec.); [α]$_D$ –59.4 (c 0.17, MeOH); UV (H$_2$O) λ$_{max}$ 250.0 nm (ε 15800) (pH 2), 250 0 nm (ε 14600) (pH 7), 254.0 nm (ε 15900)(pH 11).

1-(3,5-Di-O-acetyl-2-deoxy-2-fluoro-β-L-ribofuranosyl) uracil (13). To a suspension of 2,2'-anhydro-L-uridine (17.0 g, 0.075 mol)[163] in DMF (300 mL) and 3,4-dihydropyran (180 mL) at 0° C. was added p-toluenesulfonic acid (14.0 g) and the mixture was stirred at 0° C. for 4 h when a clear solution was obtained. It was neutralized with Et$_3$N (30 mL) and then evaporated to dryness. The residue was redissolved in EtOAc, washed with sat. NaHCO$_3$ and dried (MgSO$_4$). Removal of solvent gave a residue which was triturated wuth hexanes and filtered. The filter cake was washed with hexanes and dried to give protected 2,2'-anhydro-L-uridine as a white solid of 27.5 g (93%), which suspension (23.0 g, 58.5 mmol) in MeOH (300 mL) and 1 N NaOH (100 mL) was stirred at rt for 2 h, the neutralized with dilute acetic acid. The mixture was evaporated to dryness and the residue was loaded to a silica gel pad, eluted with EtOAc to give 12 as a white solid of 22.6 g (94%): UV (MeOH) λ$_{max}$ 263.0 nm;

To a stirred mixture of 12 (20.6 g, 0.05 mol) in CH$_2$Cl$_2$ (300 mL) and pyridine (50 mL) at –60° C. was added DAST (25.0 g, 0.155 mol) under N$_2$. It was slowly warmeed up to rt and then refluxed for 4H. The reaction was quenched by sat. NaHCO$_3$ and ice-water, then extracted with CH$_2$Cl$_2$ (100 mL×3), washed with sat. NaHCO$_3$ and dried (MgSO$_4$). Removal of solvent gave a dark-brown syrup (18.9 g), which was redissolved in MeOH (300 mL). To this was added p-toluenesulfonic acid (6 g) and the mixture was stirred at rt for 3 h. It was neutralized with pyridine (50 mL), coevaporated with pyridine (2×50 mL), then redissolved in pyridine (100 mL). To this was added Ac$_2$O (20 mL) and the mixture was stirred at rt for 20 h. Removal of solvent and recrystallization from EtOH gave 13 as a white solid of 6.8 g (total 41%): WV (MeOH) λ$_{max}$ 257.0 nm; $^1$H NMR (CDCl$_3$) δ 8.62 (s, 1H, NH, D$_2$O exchangeable), 7.33 (d, 1H, H-6, j=8.1 Hz), 5.72 (dd, 1H, H-1', J$_{1',2'}$=2.0 Hz, J$_{1',F}$=25.0 Hz), 5.70 (d, 1H, H-5, J=8.1 Hz), 5.30 (ddd, 1H, H-2', J$_{2',F}$=52.2 Hz), 5.08 (ddd, 1H, H-3', J$_{3',F}$=17.9 Hz), 4.31 (m, 3H, H-4', H-5'), 2.07, 2.03 (2s, 6H, Ac).

5-Iodo-2'-deoxy-2'-fluoro-β-L-uridine (14). A mixture of 13 (3.3 g, 0.01 mol) and ICl (2.4 g, 0.015 mol) in CH$_2$Cl$_2$ (100 mL) was stirred at reflux for 5 h. It was then diluted with CH$_2$Cl$_2$ (150 mL), washed successively with NaHSO$_3$ (100 mL×3), sat. NaHCO$_3$ (50 mL×2), and dried (MgSO$_4$). Removal of solvent gave protected FIRU as a white foam of 4.1 g (90%), which was treated with NaOMe/MeOH. Trituation in ether followed by recrystallization from water gave 14 as a white solid: mp 217–218° C.; [α]$_D$ +9.41 (c 0.36, MeOH); UV (H$_2$O) λ$_{max}$ 285.5 nm (ε 8660) (pH 1), 283.5 nm (ε 809) (pH 7), 277.0 nm (ε 6450) (pH 11); $^1$H NMR (DMSO-d$_6$) δ 11.75 (s, 1H, NH, D$_2$O exchangeable), 8.54 (1H, H-6), 5.86 (bd, 1H, H-1', J$_{1',F}$=16.8 Hz), 5.62 (d, 1H, 3'-OH, D$_2$O exchangeable), 5.41 (t, 1H, 5'-OH, D$_2$O exchangeable), 5.04 (dd, 1H, H-2', J$_{2',F}$=53.1 Hz), 4.18 (dm, 1H, H-3', J$_{3',F}$=23.4 Hz), 3.90 (m, 1H, H-4'), 3.72 (m, 2H, H-5'); Anal. Calcd. for C$_9$H$_{10}$FIN$_2$O$_5$: C, 29.05; H, 2.71; N, 7.53. Found; C, 29.11; H, 2.85; N, 7.33.

E-5-(2-Methoxycarbonylvinyl)-1-(2-deoxy-2-fluoro-β-L-ribofuranosyl) uracil (15). A mixture of Pph3 (125 mg, 0.47 mmol), Pd(Oac)2 (63 mg, 0.25 mmol), Et$_3$N (1.25 mL) in 1,4-dioxane (3 mL) was stirred under reflux for 10 min., then cooled down to just under reflux. To this was added methyl acrylate (1.13 mL, 12.6 mmol) followed by 14 (930 mg, 2.50 mmol) and 1,4-dioxane (10 mL). The mixture was refluxed for 0.5 h, then filtered through a Celite pad, and washed with dioxane. The combined filtrate was evaporated to dryness and the residue was purified by silica gel column chromatography (9:1 CHCl$_3$:MeOH) to give an off-white foam 15 (630 mg, 76%): UV (MeOH) λ$_{max}$ 299 264.0 nm (sh); $^1$H NMR (CDCl$_3$) δ 11.73 (s, 1H, NH, D$_2$O exchangeable), 8.51 (s, 1H, H-6, j=8.1 Hz) 7.29 (d, 1H, Ha, J=15.9 Hz), 6.79 (d, 1H, Hb, J=15.9 Hz), 5.88 (d, 1H, H-1', J$_{1',F}$=16.9 Hz), 5.62 (d, 1H, 3'-OH, D$_2$O exchangeable), 5.48 (t, 1H, 5'-OH, D$_2$O exchangeable), 5.04 (dd, 1H, H-2', J$_{2',F}$=52.8 Hz), 4.16 (dm, 1H, H-3', J$_{3',F}$=24.3 Hz), 3.90 (m, 3H, H-4'), 3.72 (m, 2H, H-5'), 3.68 (s, 3H, COOMe).

E-5-(2-Carboxyvinyl)-I-(2-deoxy-2-fluoro-β-L-ribofuranosyl) uracil (16). Compound 15 (560 mg, 1.70 mmol) was stirred in a NaOH solution (2 N, 5 mL) at rt for 1.5 h, then diluted with water (20 mL) and neutralized with Dowex 50 w×8 (H$^+$) resin. The mixture was filtered and washed with water and acetone. The combined filtrate was evaporated to dryness to give a pale-white solid, which was triturated with Et$_2$O to give 16 as an off-white solid (450 mg, 84%): UV (MeOH) λ$_{max}$ 298.0,0 267.0 mn (sh); $^1$H NMR (CDCl$_3$) δ 11.70 (s, 1H, NH, D$_2$O exchangeable), 8.49 (s, 1H, H-6, j=8.1 Hz 7.22 (d, 1H, Ha, J=15.9 Hz), 6.73 (d, 1H, Hb, J=15.9 Hz), 5.89 (d, 1H, H-1', J$_{1',F}$=16.8 Hz), 5.86 (d, 1H, 3'-OH, D$_2$O exchangeable), 5.62 (bs, 1H, 5'-OH, D$_2$O exchangeable), 5.05 (dd, 1H, H-2', J$_{2',F}$=52.9 Hz), 4.18 (dm, 1H, H-3', J$_{3',F}$=24.1 Hz), 3.89 (m, 3H, H-4'), 3.74 (m, 2H, H-5').

E-5-(2-Bromovinyl)-1-(2-deoxy-2-fluoro-β-L-ribofuranosyl) uracil (17). To a suspension of compound 16 (190 mg, 0.6 mmol) and KHCO$_3$ (240 mg, 2.4 mmol) in DMF (10 mL) was added N-bromosuccinimide (130 mg, 0.72 mmol). The mixture was stirred at rt for 5 h and then evaporated to dryness. The residue was purified on a silica gel column (9:1 CHCl$_3$:MeOH) followed by preparative TLC (9:1 CHCl$_3$:MeOH). Coevaporation of the product with Et$_2$O gave as a white solid of 90 mg (43%): mp80–83° C.; [α]$_D$+14.43 (c 0.2, MeOH); UV (H$_2$O) λ$_{max}$ 249.0 (ε 13100), 290.0 nm (ε 9660) (pH 1), 249 (ε 11500), 292.5 nm (ε 8810) (pH 7), 249.0 (ε 13800), 290.0 nm (sh) (pH 11).

(2S,5R)-E-5-(2-Bromovinyl)-1-(1'R,2'S,5'R)-menthylcarboxyl-1,3-oxathiolan-5-yl)uracil (19). To a suspension of (E)-5-bromovinyluracil (257 mg, 1.18 mmol) in CH$_2$Cl$_2$ (3 mL) were added TBDMSOTf (0.72 mL, 3.13 mmol) and 2,4,6-collidine (0.42 mL, 3.11 mmol) at rt. The reaction mixture was stirred for 30 min. To the resulting solution was slowly added dropwise a solution of 18 (362 mg, 1.15 mmol) in CH$_2$Cl$_2$ (8 mL) followed by TMSI (0.19 mL, 1.3 mmol). The mixture was stirred at rt for 3 h and then quenched with sat. Na$_2$S$_2$O$_3$ solution. The organic layer was washed with brine, dried (MgSO$_4$), filtered, and concentrated. The residue was chromatographed on a silica gel (hexanes:EtOAc, 3:1) to a white solid as anomeric mixtures (β:α=30:1 by $^1$H NMR), which was recrystallized from EtOAc and hexanes to give 19 (500 mg, 87%) as a white solid: mp 128–129° C.; [α]$_D$ +6.6 (c 0.28, CHCl$_3$); UV (MeOH) λ$_{max}$ 248.5, 292.0 nm; $^1$H NMR (CDCl$_3$) δ 8.47 (s, 1H, H-6), 7.41 (d, H$_a$, J=13.7 Hz), 6.78 (d, 1H, H$_b$, J=13.7 Hz), 5.46 (s, 1H, H-2'), 4.85–4.78 (m, 1H, H-5'), 3.43 (dd, 1H, H-4', J=12.1, 4.7 Hz), 3.16 (dd, 1H, H-4', J=12.1, 7.5 Hz), 2.06–1.40 (m, 7H), 1.15–1.00 (m, 2H), 0.96–0.91 (m, 6H), 0.81 (d, 3H, J=6.8 Hz); Anal. Calcd. for $C_{20}H_{27}BrN_2O_4S\cdot 0.1C_6H_{14}$: C, 49.88; H 5.77; N, 5.65; S, 6.35; Br, 15.83. Found; C, 49.59; H, 5.99; N, 5.46; S, 6.26; Br, 15.85.

(2S,5R)-E-5-(2-Bromovinyl)-1-(2-hydroxymethyl-1,3-oxathiolan-5-yl)uracil (20). To a solution of 19 (153 mg, 0.313 mmol) in 10 mL of EtOH, NaBH$_4$ (24 mg, 0.626 mmol) was added portion at 0° C. and the mixture was stirred at rt for 6 h. At that time, NaBH$_4$ (24 mg, 0.626 mmol) was added and stired for another 6 h. The reaction mixture was neutralized with HOAc and extracted with CH$_2$Cl$_2$ (2×10 mL). The organic layer was dried (MgSO$_4$), filtered, and concentrated. The residue was prified by silica gel column chromatography (CHCl$_3$:MeOH, 30:1) to give 20 (73 mg, 70%) as a white solid, which was recrystallized from hexanes-CH$_2$Cl$_2$-MeOH: mp 155° C. (dec.); $[\alpha]_D$+ 62.4 (c 0.21, MeOH); UV (MeOH) $\lambda_{max}$ 251.0 nm ($\epsilon$ 15400), 291.5 ($\epsilon$ 13100) (pH 7), 249.0 ($\epsilon$ 16600), 292.0 nm ($\epsilon$ 12 (pH 2), 254.0 ($\epsilon$ 16600), 284.5 nm (sh) (pH 11).

(2R,5S)-E-5-(2-Bromovinyl)-1-[(1'R,2'S,5'R)-menthylcarboxyl-1,3-oxathiolan-5-yl)uracil (22). To a suspension of (E)-5-bromovinyluracil (250 mg, 1.15 mmol) in CH$_2$Cl$_2$ (2 mL) were added TBDMSOTf (0.7 mL, 2.53 mmol) and 2,4,6-collidine (0.4 mL, 2.27 mmol) at rt. The reaction mixture was stirred for 30 min. To the resulting solution was slowly added dropwise a solution of 21 (380 mg, 1.15 mmol) in CH$_2$Cl$_2$ (5 mL) followed by TMSI (0.18 mL, 1.27 mmol). The mixture was stirred at for 3 h and then quenched with sat. Na$_2$S$_2$O$_3$ solution. The organic layer was washed with brine, dried (MgSO$_4$), filtered, and concentrated. The residue was chromatographed on a silica gel (hexanes:EtOAc, 3:1) to a white solid as anomeric mixtures ($\beta$:$\alpha$=27:1 by $^1$H NMR), which was recrystallized from EtOAc and hexanes to give 22 (456 mg, 81%) as a white solid: mp 124–126° C.; $[\alpha]_D$-97.2(c 0.34, CHCl$_3$); UV (MeOH) $\lambda_{max}$ 248.5, 292.0 nm; $^1$H NMR (CDCl$_3$) δ 8.47 (s, 1H, H-6), 8.2 (s, NH), 7.42 (d, 1H, H$_a$, J=13.7 Hz), 6.78 (d, 1H, H$_b$, J=13.7 Hz), 5.46 (s, 1H, H-2'), 4.84–4.78 (m, 1H, H-5'), 3.44 (dd, 1H, H-4', J=12.1, 4.7 Hz), 3.18 (dd, 1H, H-4', J=12.1, 7.1 Hz), 2.08–1.41 (m, 7H), 1.13–0.86 (m, 8H), 0.78 (d, 3H, J=6.9 Hz); Anal. Calcd. for $C_{20}H_{27}BrN_2O_4S$: C, 49.28; H, 5.58; Br, 16.39; N, 5.75; S, 6.58. Found; C, 49.38; H, 5.67; Br, 16.47; N, 5.66; S, 6.47.

(2R,5S)-E-5-(2-Bromovinyl)-1-(2-hydroxymethyl-1,3-oxathiolan-5-yl)uracil (23). To a solution of 22 (124 mg, 0.254 mmol) in 8 mL of EyOH, NaBH$_4$ (19 mg, 0.508 mmol) was added portion at 0° C. and the mixture was stirred at rt for 6 h. At that time, NaBH$_4$ (19 mg, 0.508 mmol) was and stiired for another 6 h. The reaction mixture was neutralized with HOAc and extracted with CH$_2$Cl$_2$ (10 mL×2). The organic layer was dried (MgSO$_4$), filtered, and concentrated. The residue was prified by silica gel column chromatography (CHCl$_3$:MeOH, 30:1) to give 23 (54 mg, 64%) as a white solid, which was recrystallized from hexanes-CH$_2$Cl$_2$—MeOH: mp 154° C. (dec.); $[\alpha]_D$-60.2 (c 0.56, MeOH); UV (MeOH) $\lambda_{max}$ 250.5 ($\epsilon$ 12700), 290.0 nm ($\epsilon$ 10700) (pH 7), 249.5 ($\epsilon$ 14100), 292.5 nm 10800) (pH 2), 254.0 ($\epsilon$ 14100), 285.0 nm (sh) (pH 11).

(2R,5R)-E-5-(2-Bromovinyl)-1-[2-[[(tert-Butyldiphenylsilyl)oxyl]methyl]-1,3-dioxolan-5-yl]uracil (25) and (2R,5S)-E-5-(2-Bromovinyl)-1-[2-[[(tert-Butyldiphenylsilyl)oxy]methyl]-1,3-dioxolan-5-yl]uracil (26). To a suspension of (E)-5-bromovinyluracil (420 mg, 1.94 mmol) in CH$_2$Cl$_2$ (20 mL) were added TBDMSOTf (1.2 mL, 5.13 mmol) and 2,4,6-collidine (0.67 mL, 5.1 mmol) at rt. T reaction mixture was stirred for 30 min. To the resulting solution was slowly added dropwise a solution of 24 (775 mg, 1.94 mmol) in CH$_2$Cl$_2$ (20 mL) followed by TMSI (0.31 mL, 2.14 mmol). The mixture was stirred at rt for 3 h and then quenched with sat. Na$_2$S$_2$O$_3$ solution. The organic layer was washed with brine, dried (MgSO$_4$), filtered, and concentrated. The residue was chromatographed on a silica gel (hexanes:EtOAc, 4:1) to give $\alpha$-isomer 26 (164 mg, 15%) as a white solid and $\beta$-isomer 25 (519 mg, 48%) as a white foam, which was crystallized from CH$_2$Cl$_2$ and hexanes: 25: mp 64–66° C.; $[\alpha]$ +22.6 (c 0.46, CHCl$_3$); UV (MeOH) $\lambda_{max}$ 249.5, 293.0 nm; $^1$H NMR (CDCl$_3$) δ 8.24 (s, NH), 7.70–7.30 (10H, Ph-H), 7.32 (d, 1H, J=13.6 Hz, Ha), 6.30 (ps t, 2H, J=2.9, 1.6 Hz, H-5), 6.29 (d, 1H, J=13.6 Hz, Hb), 5.10 (ps t, 1H, H-2', J=3.4, 3.3 Hz), 4.20–4.15 (m, 2H, H-4'), 3.95 (dd, 1H, H-2", J=11.7, 3.2 Hz), 3.89 (dd, 1H, H-2", J=11.7, 3.5 Hz), 1.09 (s, 9H, $^t$Bu); Anal. Calcd. for $C_{26}H_{29}BrN_2O_5Si$: C, 56.01; H, 5.24; Br, 14.33; N, 5.02. Found; C, 55.79; H, 5.41; Br, 14.18; N, 4.98. 26: mp 148–150° C.; $[\alpha]_D$-1.7 (c 1.29, CHCl$_3$); UV (MeOH) $\lambda_{max}$ 249.5, 293.0 nm; $^1$H NMR (CDCl$_3$)δ 8. (s, NH), 7.69–7.39 (m, 10H, Ph-H), 7.28 (d, 1H, J=13.6 Hz, Ha), 6.68 (d, 1H, J=13.6 Hz, H$_b$), 6.28 (dd, 1H, H-5', J=5.2, 2.0 Hz), 5.55 (ps t, 1H, H-2', J=3.1, 2.9 Hz), 4.41 (dd, 1H, H-4', J=9.7, 5.2 Hz), 4.04 (dd, 1H, H-4', J=9.7,2.0 Hz), 3.74 (dd, 1H, J=11.7, 2.8 Hz,), 3.70 (dd, 1H, J=11.7, 3.4 Hz, H-2"), 1.07 (s, 9H, $^t$Bu); Anal. Calcd. for $C_{26}H_{29}BrN_2O_5Si$: C, 56.01; H, 5.24; Br, 14.33; N, 5.02. Found; C, 55.75; H, 5.23; Br, 14.58; N, 5.01.

(2R,5R)-E-5-(2-Bromovinyl)-1-[2-(hydroxymethyl)-1,3-dioxolan-5-yl]uracil (27). A solution of 25 (278 mg, 0.499 mmol) in CH$_3$CN (15 mL) was treated with tetra-n-butylammoniumfluorid (I M solution in THF) (0.6 mL, 0.6 mmol) at rt for 1 h. After concentration of the mixture, the residue was purified by silica gel column chromatography (CHCl$_3$:MeOH, 20:1) to give 27 (151 mg, 95 as a white solid: mp 176–177° C.; $[\alpha]_D$+6.5 (c 0.47, MeOH); UV (MeOH) $\lambda_{max}$ 249.5 ($\epsilon$ 15600), 291.0 nm 11700) (pH 7), 248.5 ($\epsilon$ 16300), 291.5 nm ($\epsilon$ 11800) (pH 2), 253.5 ($\epsilon$ 16500), 284.5 nm (sh) (pH 11).

(2R,5S)-E-5-(2-Bromovinyl)-1-[2-(hydroxymethyl)-1,3-dioxolan-5-yl]uracil (28). A solution of 26 (140 mg, 0.251 mmol) in CH$_3$CN (10 mL) was treated with tetra-n-butylammoniumfluorid (I M solution in THF) (0.3 mL, 0.3 mmol) at rt for 1 h. After concentration of the mixture, the residue was purified by silica gel column chromatography (CHCl$_3$:MeOH, 20:1) to give 28 (72 mg, 90%) as a white solid: mp 75–78° C.; $[\alpha]_D$-2.8 (c 0.4, MeOH); UV (MeOH) $\lambda_{max}$ 250.0 ($\epsilon$ 13900), 292.0 nm ($\epsilon$ 10600) (pH 7), 249.5 ($\epsilon$ 14400), 291.5 nm ($\epsilon$ 10800) (pH 2), 254.0 ($\epsilon$ 14100), 284.0 nm (sh) (pH 11).

Similar methods to synthesis of 27 and 28 were applied to synthesize dioxolane 5-(E)-halovinyluracil nucleosides from 29.

(2S,5S)-E-5-(2-Chlorovinyl)-1−12-[[(tert-Butyldiphenylsilyl)oxy]methyl]-1,3-dioxolan-5-yl]uracil (30) and (2S,5R)-E-5-(2-chlorovinyl)-1-2-[[(tert-Butyldiphenylsilyl)oxy]methyl]-1,3-dioxolan-5-yl]uracil (31). 30 (50%): white foam; $[\alpha]_D$-12.2 (c 0.29, CHCl$_3$); UV (MeOH) $\lambda_{max}$ 292.0 nm; $^1$H NMR (CDCl$_3$) δ 8 NH), 7.70–7.35 (m, 10H, Ph-H), 7.20 (d, 1H, J=13.3 Hz, Ha), 6.30 (dd, 1H, J=4.5, 2.8 Hz, H-5), 6.00 (d, 1H, J=13.3 Hz, Hb), 5.10 (ps t, 1H, H-2', J=3.41, 3.36 Hz), 4.20–4.15 (m, 2H, H-4'), 3.95 (dd, 1H, H-2", J=11.7, 3.3 Hz), 3.90 (dd, 1H, H-2", J=11.8, 3.5 Hz), 1.08 (s, 9H, $^t$Bu); Anal. Calcd. for $C_{26}H_{29}ClN_2O_5Si$: C, 60.87; H, 5.70; N, 5.46. Found; C, 61.00; H, 5.93; N, 5.29. 31 (26%): mp 62–63° C.; $[\alpha]_D$27+ 3.9 (c 0.31, CHCl$_3$); UV (MeOH) $\lambda_{max}$ 292.0 nm; $^1$H NMR (CDCl$_3$) NH), 7.69–7.27 (m, 10H, Ph-H), 7.32 (d, 1H, J=13.3 Hz, Ha), 6.40 (d, 1H, J=13.3 Hz, Hb), 6.28 (dd 1H, H-5', J=5.2, 2.0 Hz), 5.55 (ps t, 1H, H-2', J=3.1, 2.9 Hz), 4.41 (dd, 1H, H-4', J=9.7, 5.3 Hz), 4.05 (dd, 1H, H-4', J=9.7, 2.1 Hz), 3.74 (dd, 1H, J=11.6, 2.7 Hz,), 3.70 (dd, 1H, J=11.7, 3.4 Hz, H-2"), 1.07 (s, 9H, $^t$Bu); Anal. Calcd. for $C_{26}H_{29}ClN_2O_5Si \cdot H_2O$: C, 60.44; H, 5.74; N, 5.42. Found; C, 60.20; H, 5.56; N, 5.37.

(2S,5S)-E-5-(2-Bromovinyl)-1-[2-[[(tert-Butyldiphenylsilyl)oxy]methyl]-1,3-dioxolan-5-yl]uracil (32) and (2S,5R)-E-5-(2-Bromovinyl)-1-[2-[[(tert-Butyldiphenylsilyl)oxy]methyl]-1,3-dioxolan-5-yl]uracil (33). 32 (58%): mp 62–65° C.; $[\alpha]_D^{29}$ –19.0 (c 0.8, $CHCl_3$); UV (MeOH) $\lambda_{max}$ 249.5, 292.5 nm; $^1$H NMR ($CDCl_3$ 8.24 (s, NH), 7.70–7.30 (m, 10H, Ph-H), 7.32 (d, 1H, J=13.6 Hz, Ha), 6.30 (ps t, 2H, J=2.9, 1.6 Hz, H-5), 6.29 (d, 1H, J=13.6 Hz, Hb), 5.10 (ps t, 1H, H-2', J=3.4, 3.3 Hz), 4.20–4.15 (m, 2H, H-4'), 3.95 (dd, 1H, H-2", J=11.7, 3.2 Hz), 3.89 (dd, 1H, H-2", J=11.7, 3.5 Hz), 1.09 (s, 9H, $^t$Bu); Anal. Calcd. for $C_{26}H_{29}BrN_2O_5Si$: C, 56.01; H, 5.24; Br, 14.33; N, 5.02. Found; C, 56.14; H, 5.25; Br, 14.41; N, 4.92. 33 (20%): mp 147–149° C.; $[\alpha]_D$+1.4 (c 0.76, $CHCl_3$); UV (MeOH) $\lambda_{max}$ 249.5, 293.0 nm; $^1$H NMR (CD 8.21 (s, NH), 7.69–7.39 (m, 1OH, Ph-H), 7.28 (d, 1H, J=13.6 Hz, Ha), 6.68 (d, 1H, J=13.6 Hz, H$_b$), 6.28 (dd, 1H, H-5', J=5.2, 2.0 Hz), 5.55 (ps t, 1H, H-2', J=3.1, 2.9 Hz), 4.41 (dd, 1H, H-4', J=9.7, 5.2 Hz), 4.04 (dd, 1H, H-4', J=9.7, 2.0 Hz), 3.74 (dd, 1H, J=11.7, 2.8 Hz,), 3.70 (dd, 1H, J=11.7, 3.4 Hz, H-2"), 1.07 (s, 9H, $^t$Bu); Anal. Calcd. for $C_{26}H_{29}BrN_2O_5Si$: C, 56.01; H, 5.24; Br, 14.33; N, 5.02. Found; C, 55.98; H, 5.21; Br, 14.50; N, 4.92.

(2S,5S)-E-5-(2-Iodovinyl)-1-[2-[[(tert-Butyldiphenylsilyl)oxy]methyl]-1,3-dioxolan-5-yl]uracil (34) and (2S,5R)-E-5-(2-iodovinyl)-1-[2-[[(tert-Butyldiphenylsilyl)oxy]methyl]-1,3-dioxolan-5-yl]uracil (35). 34 (56%): mp 74–76° C.; $[\alpha]_D$–24.0 (c 0.23, $CHCl_3$); UV (MeOH) $\lambda_{max}$ 254.0, 298.5 nm; $^1$H NMR (CD 8.10 (s, NH), 7.71–7.37 (m, 10H, Ph-H), 7.33 (d, 1H, J=14.6 Hz, Ha), 6.64 (d, 1H, J=14.6 Hz, Hb), 6.29 (dd, 1H, J=4.3, 3.0 Hz, H-5), 5.10 (ps t, 1H, H-2', J=3.41, 3.35 Hz), 4.18 (s, 1H, H-4'), 4.17 (d, 1H, J=1.7 Hz, H-4'), 3.95 (dd, 1H, H-2", J=11.8, 3.2 Hz), 3.89 (dd, 1H, H-2", J=11.7, 3.6 Hz), 1.09 (s, 9H, $^t$Bu); Anal. Calcd. for $C_{26}H_{29}IN_2O_5Si$: C, 51.66; H, 4.84; N, 4.63. Found; C, 51.66; H, 4.92; N, 4.61. 35 (28%): mp 146–147° C.; $[\lambda]_D27$+2.3 (c 0.42, $CHCl_3$); UV (MeOH) $\lambda_{max}$ 254.0, 297.5 nm; $^1$H NMR 8.15 (s, NH), 7.69–7.40 (m, 10H, Ph-H), 7.28 (d, 1H, J=14.6 Hz, Ha), 7.02 (d, 1H, J=14.6 Hz, Hb), 6.27 (dd, 1H, H-5', J=5.1, 1.9 Hz), 5.55 (ps t, 1H, H-2', J=3.04, 2.99 Hz), 4.40 (dd, 1H, H-4', J=9.7, 5.2 Hz), 4.04 (dd, 1H, H-4', J=9.7, 1.9 Hz), 3.76–3.71 (m, 2H, H-2"), 1.07 (s, 9H, $^t$Bu); Anal. Calcd. for $C_{26}H_{29}BrN_2O_5Si$: C, 51.66; H, 4.84; N, 4.63. Found; C, 51.75; H, 4.98; N, 4.61.

(2S,5S)-E-5-(2-Chlorovinyl)-1-[2-(hydroxymethyl)-1,3-dioxolan-5-yl]uracil (36). 193–194° C.; $[\alpha]_D$–4.0 (c 0.37, MeOH); UV (MeOH) $\lambda_{max}$ 246.5 (ε 17800), 291.0 nm (ε 12500) (pH 7), 246.0 18400), 290.5 nm (ε 12500) (pH 2), 250.5 (ε 18100), 284.5 nm (sh) (pH 11).

(2S,5R)-E-5-(2-Chlorovinyl)-1-[2-(hydroxymethyl)-1,3-dioxolan-5-yl]uracil (37). mp 101–102° C.; $[\alpha]_D$+2.4 (c 0.28, MeOH); UV (MeOH) $\lambda_{max}$ 247.0 (ε 13300), 291.5 nm (ε 9550) (pH 7), 246.5 (13700), 291.5 nm (ε 9670) (pH 2), 252.0 (ε 13900), 283.0 nm (sh) (pH 11).

(2S,5S)-E-5-(2-Bromovinyl)-1-[2-(hydroxymethyl)-1,3-dioxolan-5-yl]uracil (38). 176–178° C.; $[\alpha]_D$–6.5 (c 0.27, MeOH); UV (MeOH) $\lambda_{max}$ 249.0 (ε 17000), 291.0 nm (ε 13000) (pH 7), 249.0 17200), 290.5 nm (ε 12300) (pH 2), 253.0 (ε 16700), 285.0 nm (sh) (pH 11).

(2S,5R)-E-5-(2-Bromovinyl)-1-[2-(hydroxymethyl)-1,3-dioxolan-5-yl]uracil (39). mp 76–78° C.; $[\alpha]_D$+2.5 (c 0.2, MeOH); UV (MeOH) $\lambda_{max}$ 250.5 (ε 16000), 290.0 nm (ε 12400) (pH 7), 250.0 (ε 16500), 290.0 nm (ε 12200) (pH 2), 254.5 (ε 16800), 290.0 nm (sh) (pH 11).

(2S,5S)-E-5-(2-Iodovinyl)-1-[2-(hydroxymethyl)-1,3-dioxolan-5-yl]uracil (40). mp 162° C. (dec.); $[\alpha]_D$–6.5 (c 0.27, MeOH); UV (MeOH) $\lambda_{max}$ 253.0 (ε 16000), 296.5 nm (ε 11900) (pH 1), 255.0 20700), 290.0 nm (sh) (pH 2), 255.5 (ε 16600), 290.0 nm (sh) (pH 11).

(2S,5R)-E-5-(2-Iodovinyl)-1-[2-(hydroxymethyl)-1,3-dioxolan-5-yl]uracil (41). mp 60° C. (dec.); $[\alpha]_D$+2.5 (c 0.2, MeOH); UV (MeOH) $\lambda_{max}$ 255.5 (ε 15400), 297.0 nm (ε 12400) (pH 7), 256.5 (ε 22400), 290.0 nm (sh) (pH 2), 257.5 (ε 16200), 290.0 nm (sh) (pH 11).

(2S,5S)-5-Iodo-N$^3$-p-toluoyl-1-[2-(p-toluoylhydroxymethyl)-1,3-dioxolan-5-yl]uracil (43). To a solution of 42 (208 mg, 0.61 mmol) in pyridine (10 mL) were added N-ethyldiisopropylamine (0.23 mL, 1.28 mmol) and p-TolCl (0.25 mL, 1.83 mL) and then the mixture was stirred at rt for 3 h. The reaction was quenched with water and concentrated to dryness. The residue was dissolved in EtOAc and washed with water and the organic layer was dried, filtered, and concentrated. The residue was chromatographed on a silica gel (hexane:EtOAc, 1:1) to give 43 (335 mg, 95.3%) as off-white solid: mp 166–168° C.; $[\alpha]_D$+18.1 (c 0.36, $CHCl_3$); UV (MeOH) $\lambda_{max}$ 263.5 nm NMR ($CDCl_3$) δ 8.04 (s, 1H, H-6), 7.98 (d, 2H, J=8.2 Hz), 7.78 (d, 2H, J=8.3 Hz), 7.30 (d, 2H, J=3.3 Hz), 7.28 (d, 2H, J=3.2 Hz), 6.27 (dd, 1H, H-5', J=5.5, 1.7 Hz), 5.32 (t, 1H, J=3.1 Hz, H-2'), 4.74 (dd, 1H, H-4', J=17.6, 3.3 Hz), 4.62 (dd, 1H, H-4', J=12.9, 2.9 Hz), 4.33 (dd, 1H, H-4', J=10.4, 1.7 Hz), 4.22 (dd, 1H, H-4', J=10.5, 5.6 Hz), 2.43, 2.42 (2s, 6H, $CH_3$); Anal. Calcd. for $C_{24}H_{21}IN_2O_7$: C, 50.02; H, 3.67; N, 4.86. Found; C, 50.18; H, 3.72; N, 4.85.

(2S,5S)-E-5-(2-Vinyl)-1-[2-(hydroxymethyl)-1,3-dioxolan-5-yl]uracil (44). A mixture of 45 (171 mg, 0.296 mmol), tetravinyltin (0.13 mL, 0.681 mmol), and tetrakistriphenylphosphine palladium (393 mg, 0.034 mmol) in hexamethylphosphoramide (4 mL) was stirred under $N_2$ gas at 75° C. for 24 h. After cooled to rt, water (25 mL) was added and the mixture was extracted with EtOAc (2×25 mL). The combined organic extracts were dried, filtered, and concentrated to give 44 (83.4 mg, 78.6%) as off-white solid, which was treated with saturated methanolic ammonia at rt for 24 h. After concentration, the resdue was purified by column chromatography ($CHCl_3$:MeOH, 20:1) to give 45 (31 mg, 88.8%) as a white solid: 44: UV (MeOH) $\lambda_{max}$ 284.0 nm; $^1$H NMR ($CDCl_3$) δ 8.18 (s, NH), 7.92 (d, 2H, J=8.2 Hz), 7.52 (s, 1H, 6), 7.24 (d, 2H, J=8.2 Hz), 6.37 (dd, 1H, H-5', J=5.5, 2.0 Hz), 6.08 (dd, 1H, H-, J=17.6, 11.2 Hz), 5.96 (dd, 1H, H-, J=17.6, 1.6 Hz), 5.30 (t, 1H, J=3.1 Hz, H-2'), 5.12 (dd, 1H, H-4', J=11.1, 1.6 Hz), 4.71 (dd, 1H, H-4', J=12.5, 3.2 Hz), 4.59 (dd, 1H, H-4', J=12.5, 3.1 Hz), 4.27 (dd, 1H, H-4', J=10.3, 2.1 Hz), 4.22 (dd, 1H, H-5', J=10.3, 5.5 Hz), 2.42 (s, 3H, $CH_3$) 45: mp 210–211° C.; $[\alpha]_D$–19.2 (c 0.18, MeOH); UV (MeOH) $\lambda_{max}$ 235.5 (ε 14000), 287.5 nm (ε 10300) (7), 238.5 (ε 16800), 279.5 nm (ε 13700) (pH 2), 240.5 (ε 15300), 285.0 nm (ε 7850) (pH 11).

(2S,5S)-5-Iodo-1-[2-(acetoxymethyl)-1,3-dioxolan-5-yl]uracil (46).

A solution of compound 42 (302 mg, 0.888 mmol) in pyridine was treated with DMAP (cat.) and $Ac_2O$ (0.2 mL, 2.14 mmol) was treated at rt for 2 h. The reaction was quenched by adding ice and the mixture was concentrated. The residue was dissolved in $CH_2Cl_2$ and washed with dilute HCl, sat. NaHCO$_3$, and brine. After filtration and concentration, the residue was chromatographed on a silica gel (CHCl$_3$:MeOH, 40:1) to give 46 (288 mg, 85%), which was recrystallized from CH$_2$Cl$_2$ and hexane: 234–236° C.; [λ]$_D$+10.9 (c 0.14, 50% CHCl$_3$/MeOH); UV (MeOH) λ$_{max}$ 282.5 nm; $^1$H NMR (DMSO-d$_6$) NH, D$_2$O exchangeable), 7.92 (s, 1H, H-6), 6.20 (d, 1H, H-1', J=5.5 Hz), 5.15 (s, 2H, H-2'), 4.39 (d, 1H, H-4', J=10.2 Hz), 4.34 (dd, 1H, H-4', J=13.0, 1.8 Hz), 4.30 (dd, 1H, H-4', J=13.0, 1.7 Hz), 4.11 (dd, 1H, H-4', J=10.2, 5.9 Hz); Anal. Calcd. for C$_{10}$H$_{11}$BrN$_2$O$_5$: C, 37.64; H, 3.47; Br, 25.04; N, 8.78. Found; C, 37.87; H, 3.49; Br, 25.21; N, 8.65.

(2S,5S)-5-Acetylene-1-[2-(hydroxymethyl)-1,3-dioxolan-5-yl]uracil (47). To a suspension of 46 (167 mg, 0.437 mmol), (Ph$_3$P)$_2$PdCl$_2$ (6.6 mg, 0.00934 mmol), and CuI (6.6 mg, 0.0344 mmol) in anhydrous TEA (18 mL), trimethylsilylacetylene (0.5 mL, 3.54 mmol) was added and the mixture was stirred at 50° C. for 4.5 h. After concentration, the residue was dissolved in CH$_2$Cl$_2$ and washed with 5% NaEDTA (2×50 mL) and H$_2$O. The organic layer was dried, filtered, and concentrated to a pale yellow syrup (97 mg, 63%), which was treated with 0.2 N NaOMe (5.5 mL) at rt for 2 h. The mixture was neutralized with HOAc, concentrated, and purified by column chromatography to give 47 (60 mg, 92%) as a off-white solid: mp 200° C. (dec.); [α]$_D$–12.6 (c 0.24, MeOH); UV (MeOH) λ$_{max}$ 228.0 (ε 10800), 285.5 nm (ε 13800) (pH 7), 228.0 (ε 12800), 279.5 nm (ε 16 (pH 2), 235.0 (ε 12900), 282.5 nm (ε 10500) (pH 11).

(2S,5S)-5-Ethyl-1-[2-(hydroxymethyl)-1,3-dioxolan-5-yl]uracil (48). 47 (50 mg, 0.21 mmol) was stirred in EtOH (5 mL) with 10% Pd-C (30 mg) under H$_2$ at 1 atm for 1H, th filtered and washed with EtOH. The combined filtrate was evaporated to dryness and coevaporated with ether and chromatographed on a silica gel (CHCl$_3$:MeOH, 20:1) to give 48 (49.9 mg, 98%) as a white solid: mp 132–133° C.; [α]$_D$+16.5 (c 0.64, MeOH); UV (MeOH) λ$_{max}$ 266.0 nm (ε 13000) (pH 7), 266.0 nm (ε 12300) (pH 2), 266.0 nm (ε 10500) (pH 11).

Biological Data

Anti-VZV Activity

Virus growth inhibition assay. Confluent virus permissive cells in 12-well plates are inoculated with the virus at 30–40 pfu/well. After one-hour adsorption at 37° C., the inoculum is replaced with the medium containing 10% of dialyzed FBS and tested compounds at various dosages. Each dosage is duplicated. The infected cells are harvested at 72-hour postinfection. For HSV virus, the plaque reduction assay is performed to measure the virus growth. ID$_{50}$ is designated as the dosage that inhibits 50% of plaque formation compared with untreated controls. For VZV and EBV, the infected cells are lysed by "freeze-thaw" and the lysate is treated with protease K and RNase. The DNA is then subjected to slot-blot as described previous (Yao, et al., Biochem. Pharmacol. 51: 941–947). The viral DNA is detected by hybridization with $^{32}$P-labeled DNA fragment of viral specific gene. Autoradiographic results are quantitated by Personal Densitometer SI (Molecular Dynamics., Sunnyvale, Calif.). The same membrane is stripped and rehybridized with human β-actin gene fragment. The viral DNA amount is subsequently normalized by viral DNA/human actin DNA. The concentration of the tested compounds, which inhibit 50% of viral DNA synthesis compared to untreated control, is defined as IC$_{50}$. The results of the testing described above are set forth in Table 1, below.

Anti-EBV Activity

Procedure

Cell Cultures

A high yield of EBV producing cell line H1 derived from human P3HR1 cells was used in this study. Cells were cultured in RPMI medium supplemented with 10% dialyzed fetal bovine serum and 100 μg/ml Kanamycin and were grown at 37° C. in a humidified incubator containing 5% CO$_2$.

Exposure of H1 Cells to Drugs

H1 cells were maintained in logarithmic phase of growth for two days prior to the initiation of treatment. The H1 cells were seeded in 24 well plates at the density of 2×10$^5$ cells per well in 2 ml of fresh medium with or without drug treatment and were incubated at 37° C. for 5 days. Following the period of drug treatment the cells were pelleted and used to determine the inhibitory effect of drug on EBV DNA by slot blot assay.

Slot Blot Assay

A total of 4×10$^5$ H1 cells treated with the various nucleoside analogs (as set forth below) were lysed in 400 μl of 10 mM Tris-HCl (pH 7.5) solution by freezing and thawing 3 times. The cell lysate was treated with RNAase A (at a final concentration of 50 μg/ml) at 37° C. for 30 minutes and then with proteinase K (at a final concentration of 100 μg/ml) at 55° C. for 2 hr. The samples were denatured by adjusting the final concentration to 0.4N NaOH/10 mM EDTA at pH 8.2. After heating for 10 minutes in a water bath at 100° C., the samples were spotted onto positively charged nylon membrane using a manifold. Then α-$^{32}$P-dCTP labeled EBV ECORIC fragment was used as a probe for DNA hybridization. The same membranes were reprobed with human Alu DNA (BAMH1 fragment) after stripping the EBV ECORIC probe. Autoradiographic results were anlayzed by densitometry. The amount of EBV DNA in treated H1 cells was determined according to the ratio of EBV DNA to Alu DNA in comparison with non-treatment control H1 cells. The same membranes were used for assessment of toxicity to mitochondria by rehybridization with a mitochondrial DNA probe after removing the Alu DNA probe. See, for example, Yao, et al., Antimic. Agents and Chemo., July, 1993, p. 1420–1425; Yao, et al., Biochem. Pharm., Vol. 51, 941–947 (1996) (EBVassay); Doong, et al, Proc. Natl. Acad. Sci. USA, vol. 88, 8495–8499 (October, 1991); and Bridges, et al., Biochem. Pharm., Vol. 51, 731–736 (cytotoxicity and mt DNA assays).

Cytotoxicity Data

Cell Cytotoxicity Assay. CEM cells are grown at 2.5×10$^4$ Cells per ml in RPM1 media supplemented with 20% dialyzed FBS. When cells double, they are seeded in 24-well plates at 1 ml/well. The tested drugs are added at various diluted dosage. After three-day growth at 37° C., 5% CO$_2$, the cells are harvested and counted by using Coulter counter. Cytotoxicity IC$_{50}$ is designated as the dosage that inhibits 50% of the cell growth compared to the untreated controls.

TABLE 1

Anti-VZV Activities of L-β-5'BVOddU and its analogues

| Compounds | IC$_{50}$$^1$ (μM) | | | Cytotoxicity (μM)$^2$ |
| --- | --- | --- | --- | --- |
| | VZV | HSV-1 | EBV | |
| L-β-BVOddU | 0.07 | 36 | | >100 |
| D-β-BVOddU | 26 | >50 | | >100 |

TABLE 1-continued

Anti-VZV Activities of L-β-5'BVOddU and its analogues

| Compounds | IC$_{50}$[1] ($\mu$M) VZV | HSV-1 | EBV | Cytotoxicity ($\mu$M)[2] |
|---|---|---|---|---|
| L-α-BVOddU | >30 | >50 | | >100 |
| D-α-BVOddU | >30 | >50 | | >100 |
| D-BVDU | 0.05 | | | >100 |
| L-BVDU | >100 | | | >100 |
| L-β-BVSddU | 12.5 | | >50 | >100 |
| D-ara-BVU (Sorivudine) | 0.0007 | | | >100 |
| L-β-IVOddU | 0.035 | 33 | 4.1 | >100 |
| L-α-IVOddU | >30 | >50 | | >100 |
| L-β-ClVOdd | 0.15 | 18 | | >100 |
| L-α-ClVOddU | >30 | >50 | | >100 |
| L-BVF-araU | >30 | >50 | | >100 |
| L-BV2'F-dU | >30 | >50 | | >100 |
| L-IOddU | 17 | 70 | 0.1 | >100 |
| L-BrOddU | >30 | >100 | 0.2 | >100 |
| Pencyclovir[3] | 0.14 | 18 | | >100 |
| Acyclovir[3] | 2 | 13.6 | | >100 |

[1]IC$_{50}$ is designated as the concentration that inhibits 50% of virus growth.
[2]Cytotoxicity is conducted in CEM cells.
[3]Clinically approved.

Increased Retention (Half-Life) of 5-FluoroUracil

BDF1 mice were injected p.o. with L-5-Bromovinyl Dioxolane uracil (β-L-5BVOddU), D-5 Bromovinyl Arabinoside Uracil (D-BVArU) at a concentration of 20 mg/kg or with a saline control solution. Two hours after injection, 5-Flurouracil (FU) at a concentration of 200 mg/kg was administered i.p. After one hour the mice were terminated, and the FU metabolites were determined by $^{19}$F-NMR. The control mouse showed catabolite amino acids after the -20 (ppm) area, but the D-BVArU decreased from catabolite amino acids and the L-BVOddU inhibited the catabolite amino acids almost 100%. The NMR data also showed some anabolites, possibly nucleotides, in the +(ppm) area. These results evidence that the BV analogs slow the break-down of FU. Consequently, the coadministration of any one or more of the β-L nucleoside compounds along with FU or an FU produrg in the treatment of cancer to enhance the effectiveness of these agents is meritorious and unexpected.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A method for treating a viral infection in a patient caused by Epstein-Barr virus comprising administering to said patient in need thereof a therapeutically effective amount of a compound according to the structure:

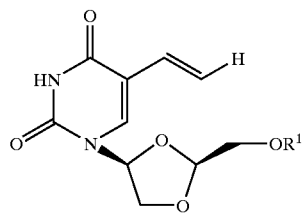

where R$^1$ is H, a C$_1$ to C$_{20}$ acyl or ether group, a phosphate, diphosphate, triphosphate or phosphodiester group.

2. The method according to claim 1 where R$^1$ is H, a C$_1$ to C$_{20}$ acyl group, a phosphate group or a phosphodiester group.

3. The method according to claim 1 where R$^1$ is H, a C$_1$ to C$_{20}$ acyl group, a phosphate group, a triphosphate group or a phosphodiester group.

4. The method according to claim 1 wherein R$^1$ is H, a phosphate group or a C$_1$ to C$_{20}$ acyl group.

5. The method according to claim 1 wherein R$^1$ is H.

6. A method for delaying the onset of an infection caused by the Epstein-Barr virus infection in a patient in need thereof comprising administering to said patient an effective amount of a compound according to the stricture:

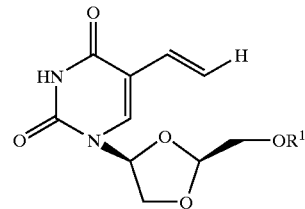

where R$^1$ is H, a C$_1$ to C$_{20}$ acyl or ether group, a phosphate, diphosphate, triphosphate or phosphodiester group.

7. The method according to claim 6 where R$^1$ is H, a C$_1$ to C$_{20}$ acyl group, a phosphate group or a phosphodiester group.

8. The method according to claim 6 where R$^1$ is H, a C$_1$ to C$_{20}$ acyl group, a phosphate group, a triphosphate group or a phosphodiester group.

9. The method according to claim 6 wherein R$^1$ is H, a phosphate group or a C$_1$ to C$_{20}$ acyl group.

10. The method according to claim 6 wherein R$^1$ is H.

11. A method for inhibiting Epstein Barr virus in a patient at risk for Epstein Bar Virus-related cancer comprising administering to said patient at risk an effective amount of a compound according to the formula:

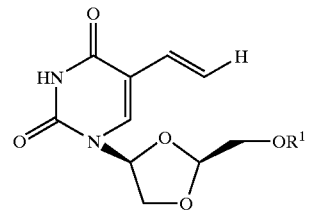

where R$^1$ is H, a C$_1$ to C$_{20}$ acyl or ether group, a phosphate, diphosphate, triphosphate or phosphodiester group.

12. The method according to claim 11 where R$^1$ is H, a C$_1$ to C$_{20}$ acyl group, a phosphate group or a phosphodiester group.

13. The method according to claim 11 where R$^1$ is H, a C$_1$ to C$_{20}$ acyl group, a phosphate group, a triphosphate group or a phosphodiester group.

14. The method according to claim 11 wherein R$^1$ is H, a phosphate group or a C$_1$ to C$_{20}$ acyl group.

15. The method according to claim 11 wherein R$^1$ is H.

16. The method according to claim 11 wherein said cancer is a lymphoma or nasopharyngeal cancer.

17. A method for treating a viral infection in a patient caused by Varicella-Zoster virus comprising administering to said patient in need thereof an effective amount of a compound according to the structure:

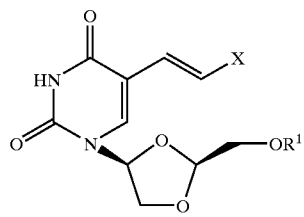

where X is Cl, Br or I; and
R$^1$ is H, a C$_1$ to C$_{20}$ acyl or ether group, a phosphate, diphosphate, triphosphate or phosphodiester group.

18. The method according to claim 17 wherein X is Br or I and R$^1$ is H, a C$_1$ to C$_{20}$ acyl group, a phosphate group or a phosphodiester group.

19. The method according to claim 17 wherein X is I and R$^1$ is H, a C$_1$ to C$_{20}$ acyl group, a phosphate group, a triphosphate group or a phosphodiester group.

20. The method according to claim 17 wherein R$^1$ is H, a phosphate group or a C$_1$ to C$_{20}$ acyl group.

21. The method according to claim 17 wherein X is Br or I and R$^1$ is H.

22. The method according to claim 21 wherein X is Br.

23. The method according to claim 21 wherein X is I.

24. A method for delaying the onset of an infection caused by the Varicella Zoster virus in a patient in need thereof comprising administering to said patient an effective amount of a compound according to the structure:

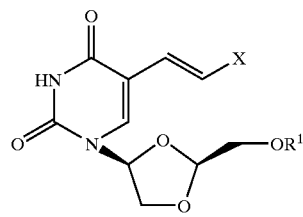

where X is Cl, Br or I; and
R$^1$ is H, a C$_1$ to C$_{20}$ acyl or ether group, a phosphate, diphosphate, triphosphate or phosphodiester group.

25. The method according to claim 24 wherein X is Br or I and R$^1$ is H, a C$_1$ to C$_{20}$ acyl group, a phosphate group or a phosphodiester group.

26. The method according to claim 24 wherein X is I and R$^1$ is H, a C$_1$ to C$_{20}$ acyl group, a phosphate group, a triphosphate group or a phosphodiester group.

27. The method according to claim 24 wherein R$^1$ is H, a phosphate group or a C$_1$ to C$_{20}$ acyl group.

28. The method according to claim 24 wherein X is Br or I and R$^1$ is H.

29. The method according to claim 28 wherein X is Br.

30. The method according to claim 28 wherein X is I.

* * * * *